United States Patent
Tanaka et al.

(10) Patent No.: US 11,593,941 B2
(45) Date of Patent: Feb. 28, 2023

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Toru Tanaka, Funabashi (JP); Kiyohide Satoh, Kawasaki (JP); Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 178 days.

(21) Appl. No.: 16/997,687

(22) Filed: Aug. 19, 2020

(65) Prior Publication Data

US 2020/0380683 A1 Dec. 3, 2020

Related U.S. Application Data

(63) Continuation of application No. PCT/JP2019/006187, filed on Feb. 20, 2019.

(30) Foreign Application Priority Data

Feb. 28, 2018 (JP) .............................. JP2018-034984

(51) Int. Cl.
*G06T 7/00* (2017.01)
*G06T 5/50* (2006.01)
(Continued)

(52) U.S. Cl.
CPC .............. *G06T 7/0014* (2013.01); *G06T 5/50* (2013.01); *G06V 10/25* (2022.01); *G06V 10/443* (2022.01); *G06V 10/751* (2022.01)

(58) Field of Classification Search
CPC .. G06T 7/001; G06T 5/50; G06T 7/70; G06T 2207/30168; G06T 7/254;
(Continued)

(56) References Cited

U.S. PATENT DOCUMENTS 6,904,163 B1   6/2005 Fujimura et al.
2004/0086168 A1*  5/2004 Kuwabara ............... G06T 7/001
                                                    382/145
(Continued)

FOREIGN PATENT DOCUMENTS

JP   2001-078996 A   3/2001
JP   2018-038815 A   3/2018
JP   2019-046057 A   3/2019

OTHER PUBLICATIONS

An Automated System for the Registration and Comparison of Photographic Images in Medicine—1988 (Year: 1988).*

(Continued)

*Primary Examiner* — Nizar N Sivji
(74) *Attorney, Agent, or Firm* — Canon U.S.A., Inc. IP Division

(57) ABSTRACT

An image processing apparatus acquires a first pixel size and a second pixel size that are pixel sizes in a predetermined axis direction of a first image and a second image captured at different points in time, respectively, determines whether the first pixel size and second pixel size differ from each other, and decides, if the first pixel size differs from the second pixel size, a size in a predetermined axis direction of a comparison area based on a larger one of the first pixel size and the second pixel size. The comparison area includes a plurality of gray levels, and is compared to a gray level of a position of interest in one of the first and second image, and the comparison area existing in the other of the first and second image, different from the one image.

28 Claims, 19 Drawing Sheets

(51) Int. Cl.
  *G06V 10/25*  (2022.01)
  *G06V 10/44*  (2022.01)
  *G06V 10/75*  (2022.01)

(58) Field of Classification Search
  CPC .......... G06T 2207/10016; G06T 7/136; G06T 7/337; G06T 7/0014; G06T 2207/30004; G06T 1/00; G06V 10/25; G06V 10/751; G06V 20/698; G06V 20/80; G06V 20/695; G06V 10/443; G06V 2201/03; A61B 6/03
  See application file for complete search history.

(56) References Cited

U.S. PATENT DOCUMENTS

| | | | |
|---|---|---|---|
| 2009/0074276 A1 | 3/2009 | Doi et al. | |
| 2011/0026773 A1* | 2/2011 | Sumitomo | G06T 1/00 382/106 |
| 2013/0044940 A1* | 2/2013 | Cohen | G06T 7/11 382/199 |
| 2013/0114862 A1* | 5/2013 | Hohjoh | G06V 10/75 382/165 |
| 2016/0205380 A1* | 7/2016 | Inoue | H04N 5/23296 348/46 |
| 2017/0301093 A1* | 10/2017 | Nakagomi | G06T 5/50 |

OTHER PUBLICATIONS

Yoshinori Itai, Hyoungseop Kim, Seiji Ishikawa, Shigehiko Katsuragawa, Kunio Doi, "Development of a voxel-matching technique for substantial reduction of subtraction artifacts in temporal subtraction images obtained from thoracic MDCT." Journal of digital imaging, vol. 23, No. 1, pp. 31-38, 2010.

Itai, Yoshinori et al.; "A Method for Reducing of Subtraction Artifacts in Temporal Subtraction Image Based on Voxel Matching Method;" IEICE Technical Report.; 2008, vol. 107, No. 461, pp. 281-284.

Toru Tanaka, et al.; "Artifacts Reduction in Temporal Subtraction Images of Thick-Slice CT Images;" Medical Imaging Technology, vol. 35, No. 5, Nov. 29, 2017, pp. 257-267.

* cited by examiner

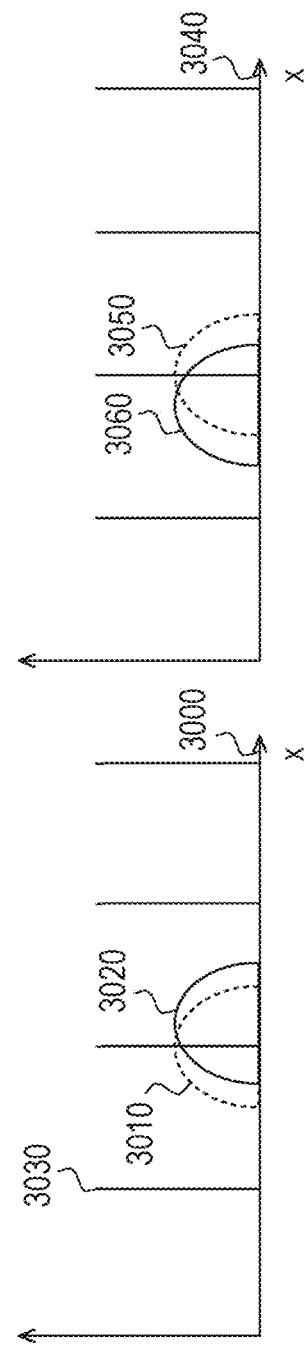

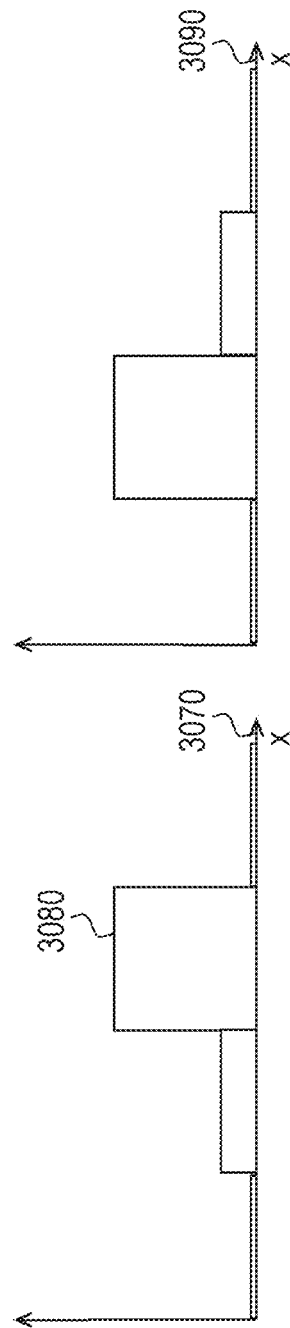

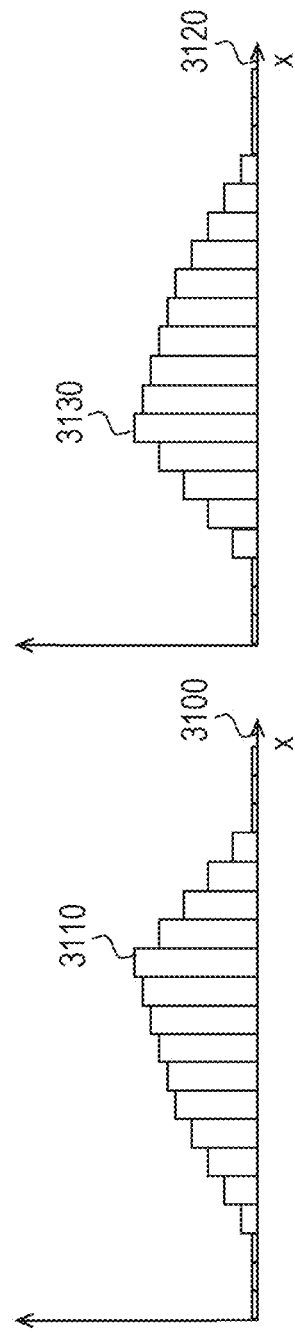

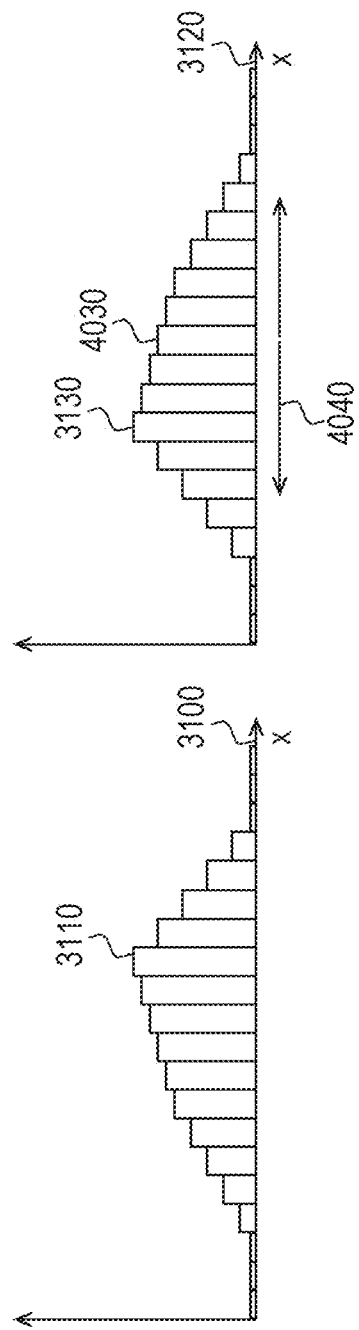

IMAGE PROCESSING APPARATUS, IMAGE PROCESSING METHOD, AND STORAGE MEDIUM

CROSS-REFERENCE TO RELATED APPLICATIONS

This application is a Continuation of International Patent Application No. PCT/JP2019/006187, filed Feb. 20, 2019, which claims the benefit of Japanese Patent Application No. 2018-034984, filed Feb. 28, 2018, both of which are hereby incorporated by reference herein in their entirety.

BACKGROUND OF THE INVENTION

Field of the Invention

The present disclosure relates to an image processing apparatus, an image processing method, and a storage medium.

Background Art

In the medical field, a difference image technique to assist comparison of two images has been known in which two images captured at different times are registered to each other, and a difference image that visualizes the difference between the images is presented. However, the technique has a problem of noise generated in the difference image due to an error in registration and the difference in gray level of the same part between the two images. To solve such a problem, NPL 1 describes a technique (a voxel matching technique) in which the difference between a pixel of interest in a first image and the corresponding pixel in a second image and the differences between the pixel of interest and a neighboring pixel of the corresponding pixel are obtained, and the smallest one of the differences is defined as the gray level. According to the technique, from among the neighboring pixels of the corresponding pixel, the pixel having a value closest to the value of the pixel of interest is selected, and the difference value between the value of the selected pixel and the value of the pixel of interest is employed. Consequently, the noise in the difference image can be reduced.

CITATION LIST

Non Patent Literature

NPL 1: Yoshinori Itai, Hyoungseop Kim, Seiji Ishikawa, Shigehiko Katsuragawa, Kunio Doi, "Development of a voxel-matching technique for substantial reduction of subtraction artifacts in temporal subtraction images obtained from thoracic MDCT." Journal of digital imaging, vol. 23, No. 1, pp. 31-38, 2010.

However, in the voxel matching method according to NPL 1, the user determines, as desired, the range of a comparison area in which the gray level of the pixel of interest in the first image is compared with each of the gray levels of the corresponding pixel and the neighboring pixels in the second image. For this reason, in some cases, the noise is not reduced sufficiently or, conversely, necessary signals are deleted. That is, the appropriate size of the comparison area cannot be determined, which is problematic.

It is to be noted that in addition to the above-described problem, a problem of the present disclosure is that the operation and effect that are derived from the configurations in "DESCRIPTION OF EMBODIMENTS" described below and that are not obtained from existing techniques are provided.

SUMMARY OF THE INVENTION

According to the present invention there is provided an image processing apparatus comprising: a pixel size acquisition unit configured to acquire a first pixel size and a second pixel size that are pixel sizes in a predetermined axis direction of a first image and a second image captured at different points in time, respectively; a determination unit configured to determine whether the first pixel size and the second pixel size acquired by the pixel size acquisition unit differ from each other; and a decision unit configured to, if the first pixel size differs from the second pixel size, decide, on the basis of a larger one of the first pixel size and the second pixel size, a size in a predetermined axis direction of a comparison area including a plurality of gray levels, the comparison area being compared to a gray level of a position of interest in one of the first image and the second image, and the comparison area existing in the other of the first image and the second image, different from the one image.

Further features of the present invention will become apparent from the following description of exemplary embodiments with reference to the attached drawings.

BRIEF DESCRIPTION OF THE DRAWINGS

FIG. 3A is a diagram illustrating an example of the shift of a discretized position according to the first embodiment.

FIG. 3B is a diagram illustrating an example of the shift of a discretized position according to the first embodiment.

FIG. 3C is a diagram illustrating an example of the shift of a discretized position according to the first embodiment.

FIG. 4 is a diagram illustrating an example of a technique for setting a comparison area according to the first embodiment.

DESCRIPTION OF THE EMBODIMENTS

Preferred embodiments of an image processing apparatus according to the present disclosure is described in detail below with reference to the accompanying drawings. Note that the scope of the invention is not limited to the illustrated examples.

EMBODIMENTS

First Embodiment

An image processing apparatus according to the present embodiment is an apparatus that generates a three-dimensional difference image between a plurality of three-dimensional images (a first image and a second image). To calculate the difference in detail between the images, the image processing apparatus according to the present embodiment converts the resolution of each of the first image and the second image so that the pixel size (voxel size) differs from that of the original image. In this way, a first converted image and a second converted image are obtained. Thereafter, a corresponding position in the second converted image that corresponds to the position of interest in the first converted image is acquired, and a comparison area is set in the second converted image with the corresponding position located at the center. At this time, the size of the comparison area is determined on the basis of the pixel sizes of the first image and the second image before resolution conversion by utilizing the fact that the position of the pixel at which the original imaging signal is most reflected is shifted by up to the half pixel size due to a shift of the discretized position between the images to be compared. Subsequently, the difference at the position of interest is calculated on the basis of the gray level at the position of interest in the first converted image and the gray levels of the plurality of pixels in the comparison area set around the corresponding position in the second converted image. Thereafter, a three-dimensional difference image is generated such that the calculated value is the grey level at the position of interest in the three-dimensional difference image. As a result, by calculating the difference value from a comparison area of the minimum necessary size, the user can observe a three-dimensional difference image with reduced noise caused by a shift of discretized position, without eliminating the signal necessary for diagnosis, such as the difference due to a change over time, as much as possible. The configuration and processing according to the present embodiment are described below with reference to FIGS. 1 to 4.

Figure 1:
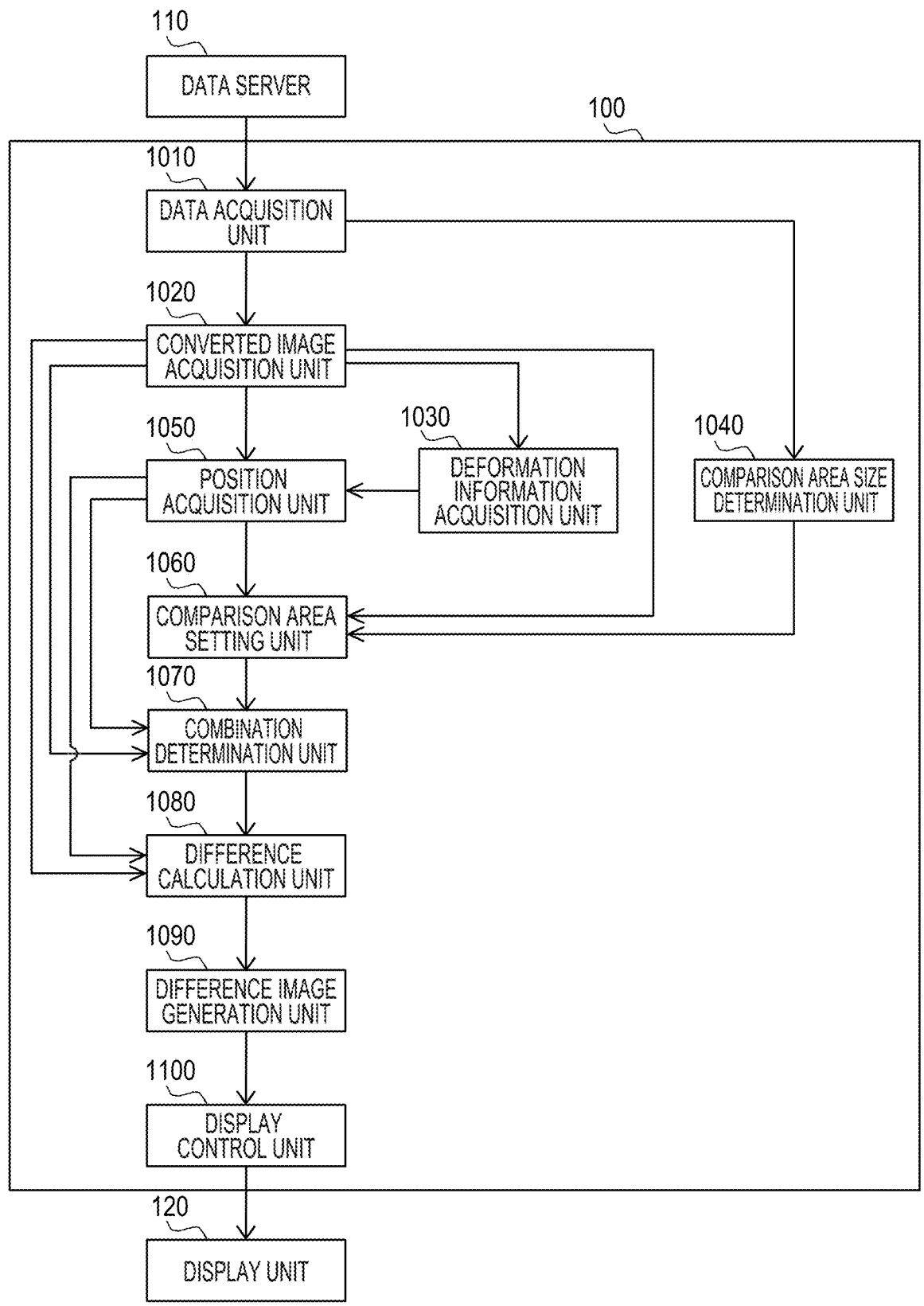
FIG. 1 is a diagram illustrating an example of the device configuration of an image processing apparatus according to a first embodiment.

FIG. 1 illustrates the configuration of a diagnostic imaging system according to the present embodiment. As illustrated in FIG. 1, an image processing apparatus 100 according to the present embodiment is connected to a data server 110 and a display unit 120. The diagnostic imaging system may include a modality (an image capture device), and an image captured by the modality may be transmitted to the image processing apparatus without passing through the data server. In this case, the data server need not be included in the system.

The data server 110 holds a first image and a second image designated by the user as the targets for generating a difference image. The first image and the second image are three-dimensional tomographic images (volume data) obtained by capturing the image of an object by the same modality under different conditions (the date and time, contrast condition, imaging parameter, etc.). The modality that captures a three-dimensional tomographic image may be an MRI apparatus, an X-ray CT apparatus, a three-dimensional ultrasonic imaging apparatus, a photoacoustic tomography apparatus, a PET/SPECT, an OCT apparatus, or the like. Furthermore, the first image and the second image may be images of the same patient in the same position captured at different dates and times with the same modality for follow-up observation or images of the same patient captured under different imaging conditions or with different imaging parameters. Alternatively, the first image and the second image may be obtained by capturing the images of different patients. Still alternatively, the first image and the second image may be the image of a patient and a reference image. The first image and the second image are input to the image processing apparatus 100 via a data acquisition unit 1010.

The display unit 120 is a monitor that displays an image generated by the image processing apparatus 100. More specifically, the display unit 120 is a monitor that displays a difference image generated using the calculated difference values as gray levels.

The image processing apparatus 100 is composed of constituent elements described below. The data acquisition unit 1010 acquires the first image and the second image input to the image processing apparatus 100. A converted image acquisition unit 1020 acquires a first converted image having a resolution converted from that of the first image and a second converted image having a resolution converted from that of the second image. A deformation information acquisition unit 1030 acquires deformation information indicating the correspondence relationship between the positions in the first converted image and the second converted image. A comparison area size determination unit 1040 determines the size of the comparison area on the basis of the pixel size of each of the first image and the second image. A position acquisition unit 1050 acquires the position of interest in the first converted image and acquires a corresponding position in the second converted image, which corresponds to the pixel of interest in the first converted image, by using the deformation information acquired by the deformation information acquisition unit 1030. A comparison area setting unit 1060 sets a comparison area having the size of a comparison area around the corresponding position in the second converted image. A combination determination unit 1070 determines a combination of the gray level at the position of interest in the first converted image and the gray levels at a plurality of positions in the comparison area of the second converted image as the target of a comparison process (calculation of the difference). A difference calculation unit 1080 calculates the difference value at the position of interest on the basis of the combination of gray levels determined by the combination determination unit 1070, that is, the gray level of the pixel of interest in the first converted image and the gray levels of a plurality of pixels in the comparison area of the second converted image. A difference image generation unit 1090 generates a difference image such that the gray level at the position of interest is the calculated difference value. A display control unit 1100 performs display control so that the first image, the second image, and the difference image are arranged side by side and displayed on the display unit 120.

Figure 2:
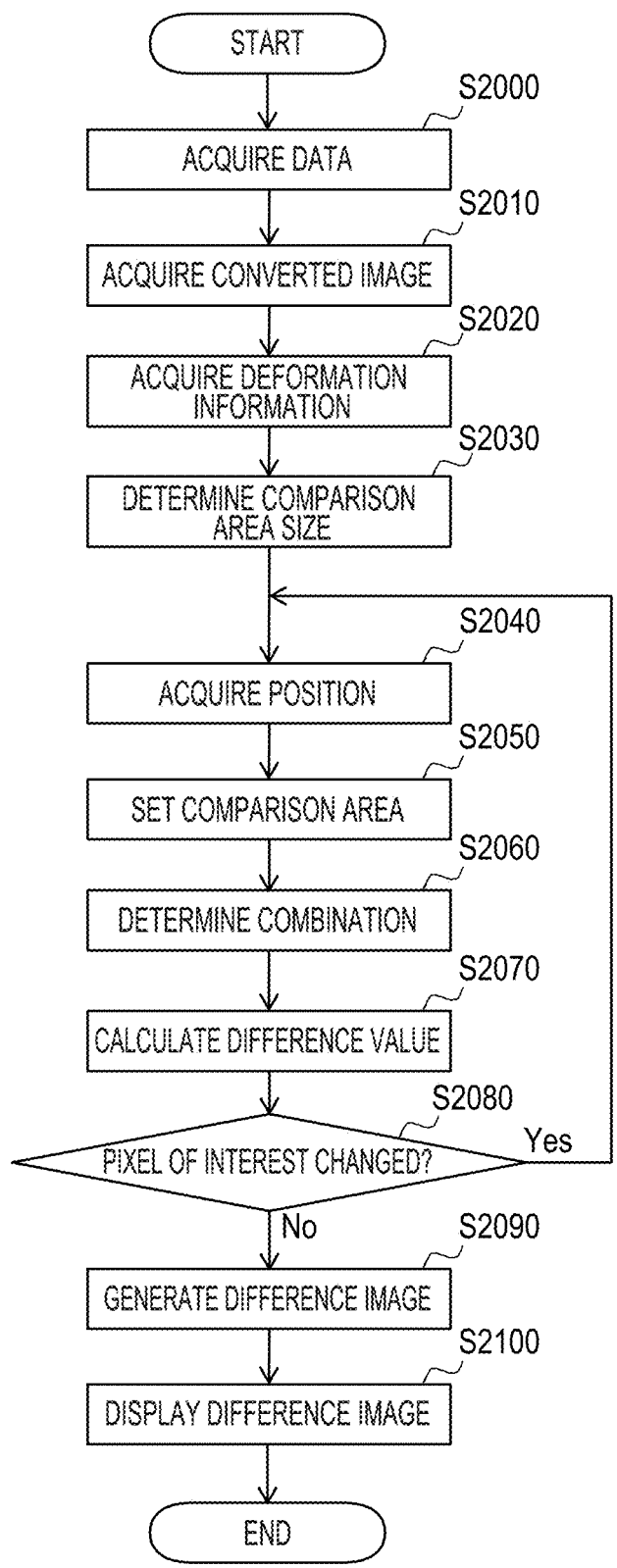
FIG. 2 is a flow diagram illustrating an example of the overall processing procedure according to the first embodiment.

FIG. 2 is a flowchart of the overall processing procedure performed by the image processing apparatus 100.

(S2000) (Data Acquisition)

In step S2000, the data acquisition unit 1010 acquires the first image and the second image input to the image processing apparatus 100. Thereafter, the data acquisition unit 1010 outputs the acquired first image and second image to the converted image acquisition unit 1020. In addition, the data acquisition unit 1010 outputs information regarding the pixel sizes of the first image and the second image to the comparison area size determination unit 1040.

(S2010) (Acquisition of Converted Image)

In step S2010, the converted image acquisition unit 1020 acquires the first converted image having a resolution converted from that of the first image so that the pixel sizes are changed and the second converted image having a resolution converted from that of the second image so that the pixel sizes are changed. For example, if the pixel size of the original image is anisotropic, an image with an isotropic pixel size is acquired so that highly accurate registration between the images can be performed in a subsequent process. For example, if the first image and the second image are widely used CT images, the resolution in a slice plane is high with respect to the distance between the slices. Accordingly, the pixels located in the inter-slice direction is subjected to up-sampling in accordance with the resolution in the slice plane. Similarly, if the pixel sizes of the first image and the second image are not the same, the resolution of at least one of the images is converted so that the pixel sizes of the images are the same. In general, conversion is performed so that the resolution is adjusted to the higher resolution. Thereafter, the converted image acquisition unit 1020 outputs the generated converted image to the deformation information acquisition unit 1030, the position acquisition unit 1050, the comparison area setting unit 1060, the combination determination unit 1070, and the difference calculation unit 1080.

Note that if the resolution conversion process is not needed (for example, if the pixel sizes of the first image and the second image are isotropic and the same), the process of this step is not performed, and the original image is considered as the converted image. Thereafter, the subsequent processing is performed.

Note that according to the present embodiment, a widely used image processing technique can be used for the interpolation of the gray level at the time of converting the resolution. For example, nearest neighbor interpolation, linear interpolation, or cubic interpolation can be used.

(S2020) (Acquisition of Deformation Information)

In step S2020, the deformation information acquisition unit 1030 acquires the deformation information so that the pixels representing the same part of the first converted image and the second converted image substantially match each other. That is, a registration process between the first converted image and the second converted image (a deformation estimation process) is performed. Thereafter, the deformation information acquisition unit 1030 outputs the acquired deformation information to the position acquisition unit 1050. That is, if the first converted image is used as a reference image, the deformation information acquisition unit 1030 acquires deformation information between the reference image and the second conversion image.

According to the present embodiment, the deformation information is acquired by a widely used image processing technique. For example, the deformation information is acquired by deforming one image so that the image similarity between the images increases after deformation. As the image similarity, a widely used technique, such as widely used Sum of Squared Difference (SSD), mutual information amount, or cross-correlation coefficient, can be used. As a model of image deformation, a widely used deformation model, such as a deformation model based on a radial basis function (e.g., Thin Plate Spline (TPS)), Free Form Deformation (FFD), or a Large Deformation Diffeomorphic Metric Mapping (LDDMM), can be used. Note that if there is only a difference in position and orientation between the first image and the second image (the two images can be approximated as such), rigid body registration between the images may be performed, and the conversion parameters of the position and orientation may be obtained as the deformation information. Alternatively, affine transformation parameters between images may be obtained as the deformation information. If there is no positional shift between images (the images can be approximated as such), the process of this step is not needed.

(S2030) (Determination of Comparison Area Size)

In step S2030, the comparison area size determination unit 1040 determines the size of the comparison area used to calculate the difference value on the basis of the pixel size of the first image and the pixel size of the second image. Thereafter, the comparison area size determination unit 1040 outputs the determined size of the comparison area to the comparison area setting unit 1060.

According to the present embodiment, to determine the size of the comparison area, the following characteristics are used. That is, due to a shift of the discretized position between a first image and a second image during image generation, the position of the pixel at which the original imaging signal of an object is most reflected is shifted between the first converted image and the second converted image by up to the sum of the half pixel sizes of the pixels of the original images. That is, the sum of the half pixel sizes of the first image and the second image is selected as the size of the comparison area.

FIG. 3 is a diagram illustrating how the shift between the observed values of the same part of the object occurs due to the discretized position shift between the images. In FIG. 3A, graphs 3000 and 3040 illustrate how the imaging signal is generated when the imaging position of the object is shifted from the modality in one direction and in the other direction, respectively. The ordinate represents the signal value when the image of the object is captured with the modality, and the abscissa represents the position in the x-axis direction. Signals 3020 and 3060 are acquired by capturing the image of the same object, and signals 3010 and 3050 denoted by dotted lines indicate the same position on the x-axis. Here, signals 3010 and 3050 are signals when the images are captured at the same position. For convenience, the position is referred to as a reference position. FIG. 3A suggests that when the images are generated from the signals 3020 and 3060 acquired from the same object, the discretized positions are shifted from the reference position in different directions. In addition, lines 3030 arranged at equal intervals in FIG. 3A indicate boundary positions of discretization. When an image is generated, the signals indicated by 3020 and 3060 are gathered in a region divided by lines to generate one pixel.

In FIG. 3B, a graph 3070 represents information regarding pixels generated by discretizing the signal 3020 illustrated in FIG. 3A. The ordinate represents the gray level, and the abscissa represents the position in the x-axis direction. For example, a pixel 3080 in FIG. 3B is a pixel generated from a region including a large amount of the signal 3020. The pixel 3080 has a high gray level. Similarly, in FIG. 3B, a graph 3090 represents information about pixels generated by discretizing the signal 3060. The ordinate represents the gray level, and the abscissa represents the position in the x-axis direction. At this time, as described above, the discretized positions of the signals 3020 and 3060 are shifted in different directions, so that the gray levels at the same position are different between the graphs 3070 and 3090.

In FIG. 3C, graphs 3100 and 3120 represent the gray levels and positions of pixels obtained by resolution-converting the pixels in the graphs 3070 and 3090 illustrated in FIG. 3B, respectively. That is, the graphs 3070 and 3090 can be regarded as the graphs of the signal values of the first image and the second image, respectively. The graphs 3100 and 3120 can be regarded as the graphs of the signal values of the first converted image and the second converted image, respectively. At this time, pixels 3110 and 3130 are the pixels that most reflect the signals 3020 and 3060 of the object, respectively. If the signals 3020 and 3060 are shifted in opposite directions, the maximum amounts of shift of the discretized positions from the reference positions 3010 and 3050 are the half pixel size of the original images, respectively. If the signals 3020 and 3060 are shifted in the opposite direction by the half pixel size, the amount of shift between the pixels 3110 and 3130 is the sum of the half pixel size of the pixel 3110 and the half pixel size of the pixel 3130.

Note that for simplicity, a one-dimensional graph only in the x-axis direction is used in FIG. 3. However, in an actual three-dimensional image, the discretized position may shift in each of the x-, y-, and z-axis directions. Accordingly, the size of the comparison area is determined on the basis of the pixel size in each of the axis directions. Note that in widely used CT images, the resolution (=the pixel sizes in the x and y directions) in a slice is sufficient and, thus, the configuration that does not perform noise reduction in the x and y directions may be employed. In this case, the size of the comparison area in the x- and y-axis directions may be set to 0, and only the size of the comparison area in the z-axis direction may be determined by the above-described technique. Alternatively, the size of the comparison area in the x- and y-axis directions may be set to a predetermined fixed value (for example, 1 mm), and only the size of the comparison area in the z-axis direction may be determined by the above-described technique. In this manner, the calculation can be sped up.

According to the present embodiment, the size of the comparison area is set to the sum of the half pixel sizes of the first image and the second image. However, the sum of the half pixel sizes of the first image and the second image may be multiplied by a predetermined constant (for example, the expected value of discretized position shift), or a predetermined constant may be added to the sum. Furthermore, the above-described predetermined constant may be changed on the basis of a method for registering the first image to the second image. For example, if registration is performed so that the difference in the gray level between the images decreases, the pixel position shift due to the discretized position shift may be corrected, and the positions of the pixels representing the same part may be closer to each other between the images. Accordingly, the predetermined constant may be reduced, and a value smaller than the maximum value of the discretized position shift may be set as the size of the comparison area. In this manner, the size of the comparison area is reduced, and an extra range is not searched. As a result, the processing speed and the accuracy can be improved. Alternatively, a value mapped by a predetermined non-linear function using the pixel sizes of the first image and the second image as input variables may be used as the size of the comparison area. Still alternatively, the size of the comparison area may be determined on the basis of only the pixel size of one of the first image and the second image. For example, the size of the comparison area may be determined on the basis of only the pixel size of the first image which is the reference image. Yet still alternatively, the size of the comparison area may be determined on the basis of the larger one of the pixel sizes of the first image and the second image. Even in this case, a value obtained by multiplying the pixel size to be used by a predetermined constant can be used as the size of the comparison area.

In addition, in the registration method in which the distance between corresponding positions (feature points) between images is reduced instead of reducing the difference in gray level, the pixel position shift due to the discretized position shift does not always decrease. In general, the accuracy of registration is high near the feature point used for registration between images, and the accuracy of registration decreases with increasing distance from the feature point. If the registration accuracy is low, the registration error may be added to the shift amount of the discretized position, which may increase the positional shift of a pixel between images. In such a case, the above-described predetermined constant may be changed for each position in the image in accordance with the distance from the feature point in the image. For example, the above-described predetermined constant may be reduced at a position near the feature point in the image and may be increased at a position away from the feature point.

(S2040) (Position Acquisition)

In step S2040, the position acquisition unit 1050 acquires the position of interest in the first converted image (the position of interest in the reference image) and acquires, in the second converted image, a corresponding position that corresponds to the position of interest by using the deformation information acquired in step S2020. That is, the position acquisition unit 1050 corresponds to an example of position acquisition means that acquires the position of interest in one image and the corresponding position that corresponds to the position of interest in the other image. Thereafter, the position acquisition unit 1050 outputs the acquired positions to the comparison area setting unit 1060, the combination determination unit 1070, and the difference calculation unit 1080.

(S2050) (Setting of Comparison Area)

In step S2050, the comparison area setting unit 1060 sets the comparison area having a size of the comparison area determined in step S2030 around the corresponding position in the second converted image. Thereafter, the comparison area setting unit 1060 outputs the information regarding the set comparison area to the combination determination unit 1070.

FIG. 4 is a diagram illustrating a comparison area set in the converted image. In FIG. 4, graph 3100 and graph 3120 represent the same graphs as the graph 3100 and graph 3120 illustrated in FIG. 3C, respectively. In FIG. 4, an example is illustrated in which the pixel size in the x-axis direction is 5 mm for both the first image and the second image, and upsampling is performed so that the pixel size is 1 mm. In this case, since the size of the comparison area in the x-axis direction is the sum of the half pixel sizes of the first image and the second image, the size of the comparison area is 2.5 mm+2.5 mm=5 mm. In FIG. 4, assume that the pixel 3110 in the first converted image is the position of interest, and the corresponding position in the second converted image (the position calculated on the basis of the deformation information) is the pixel 4030. At this time, a reference numeral 4040 designates a comparison area of a size of 5 mm set for the pixel 4030 at the corresponding position. Considering the case where the discretized position is shifted by 5 mm at the maximum in the x-axis direction, a comparison area is set to a size of 5 mm in each of the +x and −x directions from the pixel 4030. For simplicity of illustration, description has been made only for the x-axis direction. However, in an actual three-dimensional image, the comparison area is a rectangular area having a size determined on the basis of the pixel size in each of the x-, y-, and z-axis directions.

(S2060) (Determination of Combination)

In step S2060, the combination determination unit 1070 determines a combination of gray levels to be subjected to a comparison process (calculation of the difference). The combination determination unit 1070 first interpolates the gray level at the position of interest in the first converted image, which are acquired in step S2040, and the gray level of the pixel in the comparison area of the second converted image. An existing image processing technique can be used for the interpolation of the gray levels. For example, nearest neighbor interpolation, linear interpolation, or cubic interpolation can be used. Note that interpolation is not always needed. Also, note that the combination determination unit 1070 may interpolate the gray level of the pixel in the comparison area of the second converted image without interpolating the gray level at the position of interest in the first converted image. The combination determination unit 1070 may determine the combination of gray levels so that the difference is calculated between the gray level at the position of interest in the first converted image and each of the gray levels of all the pixels in the comparison area of the second converted image. Alternatively, the combination determination unit 1070 may sample at least one pixel from among the pixels included in the comparison area and determine a combination of the gray level of the pixel and the gray level at the position of interest as the combination to be subjected to difference calculation. For example, the combination determination unit 1070 samples the maximum gray level and the minimum gray level from among the pixels included in the comparison area. Thereafter, the combination determination unit 1070 determines the combination of the maximum gray level included in the comparison area and the gray level at the position of interest and the combination of the minimum gray level included in the comparison area and the gray level at the position of interest as the combinations subjected to difference calculation. Note that the gray levels to be sampled are not limited to the maximum and minimum values. Three or more values may be sampled, or one value, such as the maximum gray level or the minimum gray level, may be sampled. Alternatively, the combination determination unit 1070 may acquire a gray level range having the maximum gray level and the minimum gray level in the comparison area at both ends (the upper limit value and the lower limit value) and acquire the gray level at the position of interest and the gray level range in the comparison area as the combination to be subjected to difference calculation. Note that the gray level range in the comparison area may be other than the maximum and minimum gray levels. For example, the gray level range may be the maximum value and the minimum value after the outlier of the gray level is removed.

The combination determination unit 1070 outputs, to the difference calculation unit 1080, information indicating the determined combination of the gray levels to be subjected to difference calculation. The information indicating the combination of the gray levels output from the combination determination unit 1070 may be information indicating all the combinations of the gray level at the position of interest in the first converted image and the gray level of each of all the pixels in the comparison area of the second converted image, or only the information indicating the combination of the gray level of a pixel sampled from among the pixels included in the comparison area and the gray level at the position of interest may be output.

(S2070) (Calculation of Difference Value)

In step S2070, the difference calculation unit 1080 obtains the difference value provided to a difference image on the basis of the combination of the gray level at the position of interest in the first converted image and the gray levels in the comparison area of the second converted image determined in step S2060. The difference calculation unit 1080 calculates the difference between the gray level at the position of interest in the reference image and the gray level at each of the plurality of positions in the comparison area of the second converted image or the position having the closest gray level among gray levels of the plurality of positions. Thereafter, the difference calculation unit 1080 outputs the differences to the difference image generation unit 1090.

In FIG. 4, by calculating the difference between the gray level of the pixel 3110 of the first converted image and each of the gray levels in the comparison area 4040 of the second converted image, the difference value is acquired between the gray level of the pixel 3110 of the first converted image and the gray level of a pixel 3130 that has the minimum difference from the pixel 3110 of the first converted image. That is, the difference value of the gray level between the pixels that most reflect the signal of the object in FIG. 3 can be calculated.

According to the present embodiment, all the pixels output from the combination determination unit 1070 may be used as the pixels in the comparison area of the second converted image for calculating the difference from the gray level at the position of interest in the first converted image. Alternatively, the pixels obtained by sampling the pixels output from the combination determination unit 1070 at predetermined intervals or a predetermined number of pixels obtained by sampling the pixels at random may be used as the pixels in the comparison area. Still alternatively, the pixels in a spherical area inscribed in the comparison area may be used. In this way, the number of times the difference is calculated is reduced, and the processing can be sped up.

Furthermore, as another technique using the difference value between the gray level at the position of interest in the first converted image and the gray level of each of the pixels in the comparison area of the second converted image, the average of differences or the second smallest difference may be calculated and used as the difference value of the difference image, instead of obtaining the minimum value of the difference. According to the technique, more noise may remain than when the minimum value of the difference is obtained. However, it can be prevented from obtaining, as the minimum value, the difference from a pixel located at a non-corresponding position in the second converted image, although the pixel has a small difference from the pixel of interest in the first converted image (e.g., an artifact or a pixel of another part). As a result, it is possible to prevent the difference value from being significantly smaller than the difference from the pixel located at the corresponding position.

Alternatively, the difference value may be obtained by calculating the distribution information of the gray levels in the comparison area of the second converted image and comparing the distribution information with the gray level at the position of interest in the first converted image. For example, when the gray level range within the comparison area is acquired in step S2060, the difference value may be obtained by comparing the gray level range with the gray level at the position of interest in the first converted image. For example, if the gray level at the position of interest is included in the gray level range in the comparison area, the difference value obtained in this case may be set to 0. Alternatively, if the gray level at the position of interest is greater than the maximum value (the upper limit value) of the gray level range, the difference value from the maximum value (the upper limit value) may be used as the difference value given to the difference image. However, if the gray level at the position of interest is less than the minimum value (the lower limit value) of the gray level range, the difference value from the minimum value (the lower limit value) may be used as the difference value given to the difference image. At this time, the gray level range in the comparison area of the second converted image represents a range in which the gray level at the position of interest in the first converted image can change in accordance with the difference in the discretized position. For this reason, even if the gray levels of the same part in the images are not completely the same due to the influence of discretization and a slight difference remains, the difference can be set to 0 as long as the difference is within the range that can be changed due to a difference in discretization position. As a result, noise can be reduced more.

However, if the comparison area contains pixels having greatly different gray levels due to a lesion or an artifact, the range between the maximum and minimum gray levels in the comparison area increases and, thus, the difference at the position of interest may be wrongly set to 0. For this reason, only if the gray level at the position of interest is between the maximum value and the minimum value of the gray levels in the comparison area and if the difference between the gray level at the position of interest and each of the maximum value and the minimum value is less than or equal to a threshold value, the difference may be set to 0. Alternatively, the distribution of the gray levels in the comparison area may be classified into a plurality of clusters, and the same processing as described above may be performed on the basis of comparison of the minimum value and the maximum value of each cluster. That is, if the gray level at the position of interest is within the cluster, the difference can be set to 0. However, if the gray level at the position of interest is outside the cluster, the difference value can be set to the distance (with a sign) to the closest cluster. Note that the classification of the gray levels in the comparison area may be performed on the basis of only the gray levels or on the basis of the pixel positions and the gray levels. In the former case, for example, a clustering process can be performed on the histogram of the gray levels in the comparison area. In the latter case, for example, a clustering process can be performed through an area division process performed on the comparison area on the basis of the continuity of the gray level between pixels.

Alternatively, according to the present embodiment, instead of setting the comparison area in the second converted image, the comparison area may be set in the original second image at a position around the corresponding position. Thus, the difference between the gray level at the position of interest in the first converted image and the gray level in the comparison area of the second image may be calculated. At this time, the gray levels at a plurality of positions in the comparison area may be acquired at intervals smaller than the pixel size. The gray levels at these positions are acquired by interpolation based on the surrounding gray levels. If the interpolation technique is the same as when the second converted image is acquired in step S2010, the difference value that is equivalent to that in the case where the comparison area is set in the second converted image can be calculated.

Still alternatively, by using, as a first difference value, the difference value obtained on the basis of the gray level at the position of interest in the first converted image and the gray level of each of the pixels in the comparison area of the second converted image as described above, a difference (a second difference value) between the gray level at the position of interest in the first converted image and the gray level at the corresponding position in the second converted image may be separately obtained. Thereafter, the difference value given to the difference image may be calculated on the basis of the first difference value and the second difference value. For example, the weighted average value of the first difference value and the second difference value can be used as the difference value of the difference image. In this manner, the risk of erasing a signal that is not noise can be reduced.

(S2080) (Change Position of Interest?)

In step S2080, the position acquisition unit 1050 determines whether the difference values at all positions (all pixels) in the first converted image have been calculated. If the difference values at all positions have been calculated, the processing proceeds to step S2090. However, if the difference values at all positions have not been acquired, the processing returns to step S2040.

Note that according to the present embodiment, the difference value need not be calculated at all positions in the first converted image. The difference values may be calculated at some of the positions in the first converted image extracted in advance by an existing image processing technique. In this manner, the processing time required for noise reduction can be reduced.

(S2090) (Generation of Difference Image)

In step S2090, the difference image generation unit 1090 generates a difference image (a first difference image) having gray levels each equal to the difference value at one of the positions in the first converted image. Thereafter, the difference image generation unit 1090 stores the obtained difference image in the data server 110. Alternatively, the difference image generation unit 1090 may store the obtained difference image in a memory of the image processing apparatus 100. In addition, the difference image generation unit 1090 outputs the obtained difference image to the display control unit 1100. Note that at the same time, a widely used difference image (a second difference image) may be generated in which the second difference value calculated in step S2060 (the difference between the gray level at the position of interest in the first converted image and the gray level at the corresponding position in the second converted image) is used as the gray level.

(S2100) (Display of Difference Image)

In step S2100, the display control unit 1100 controls the display unit 120 to display the difference image (the first difference image) generated in step S2090.

As an example of a display format, for example, one screen may be divided vertically or horizontally, and the first image, the second image, and the difference image may be displayed side by side. Alternatively, the difference image (the first difference image) having a color that differs from the color of the first image or second image may be displayed in a superimposed manner, or any one of the first image, the second image, and the difference image may be selected and displayed (the selected one is displayed at the same position as desired another one). Furthermore, the resolution of one of the images may be used as a reference, and another image may be enlarged or reduced, or the images may be displayed side by side such that the corresponding position in the second image that corresponds to a pixel of interest in the first image matches the position of interest in the difference image. In addition, the first difference image and the second difference image may be switchably displayed.

As described above, the processing is performed by the image processing apparatus 100.

As described above, by calculating a difference value from the comparison area of the minimum necessary size for which a discretized position shift is taken into account, a user can observe the difference image having necessary signal remaining thereon and having reduced noise generated by the difference in gray level caused by the discretized position shift between the images.

(Modification 1-1) (Calculating Image Similarity in Consideration of Discretization Position Shift)

According to the present embodiment, to reduce noise that occurs when a difference image is generated, a method is used in which when the difference between the pixels of interest is obtained, a comparison area of a size determined on the basis of the pixel sizes is set around the pixel, and the gray levels in the comparison area are used. However, this method can also be used in other situations where comparison of pixels of interest is made. For example, in step S2020, the deformation information acquisition unit 1030 acquires the image similarity by using an existing image processing technique. This method can also be used in the process of acquiring the image similarity for image registration. That is, like SSD, when calculating the difference in the gray level between images of a certain pair, the image pair may be considered as the position of interest and the corresponding position, and the difference value may be calculated by the same processes as in step S2050, step S2060, and step S2070. In a registration process in which the deformation information is repeatedly optimized so that the image similarity increases, the similarity is evaluated between the noise-reduced image finally observed by the user in each of the optimization steps and an image acquired on the basis of the difference value calculated in a similar step. In this manner, the image similarity can be calculated in consideration of a discretized position shift. As a result, the difference image with further reduced noise can be obtained.

(Modification 1-2) (Reducing Noise at Position Specified by User)

According to the present embodiment, in step S2080, all positions (all pixels) in the first converted image or some positions extracted by an existing image processing technique in advance are used. However, the user may specify the position. That is, a noise-reduced difference image generation process may be performed for all positions or some positions within an area specified by the user in advance. Alternatively, only the second difference image may be generated and displayed, and the processes in steps S2040 to S2090 may be performed only on a nearby area of the position of interest specified interactively by the user. Thereafter, only the nearby area may be replaced with the first difference image and may be displayed. In this manner, noise can be reduced only at the minimum necessary positions and, thus, the time required for noise reduction can be reduced. Furthermore, the position determined not to be noise by the user can be excluded from the target of the noise reduction process. As a result, over-erasure of signals can be prevented.

Second Embodiment

An image processing apparatus according to the present embodiment is an apparatus that generates a three-dimensional difference image between the first image and the second image, as in the first embodiment. The image processing apparatus according to the present embodiment determines whether to perform a noise reduction process in accordance with the pixel size of an input image and generates a three-dimensional difference image by a method in accordance with the determination. As in the first embodiment, the image processing apparatus according to the present embodiment determines the size of a comparison area on the basis of the pixel sizes of a first image and a second image. At this time, if the pixel sizes of the first image and the second image are smaller than the predetermined threshold value, it is determined that the discretized position shift is small, and a difference image is generated without performing the noise reduction process. On the other hand, if the pixel size is greater than or equal to the predetermined threshold value, a difference image subjected to the noise reduction process is generated as in the first embodiment. As a result, if the discretized position shift is small, over-erasure of the difference in gray level between the images can be prevented. In addition, the processing time required for noise reduction can be reduced. The configuration and processing according to the present embodiment are described below with reference to FIGS. 1 and 5.

The configuration of the image processing apparatus according to the present embodiment is the same as that of the first embodiment. However, the comparison area size determination unit 1040 and the difference calculation unit 1080 have different functions than the first embodiment. Accordingly, the functions are described below. The other configurations have the same functions as those of the first embodiment and, thus, the descriptions of the configurations are not repeated.

The comparison area size determination unit 1040 determines whether to perform the noise reduction process on the basis of the pixel sizes of the first image and the second image. In addition, as in the first embodiment, the size of the comparison area is determined on the basis of the pixel sizes of the first image and the second image. If the noise reduction process is not performed, the difference calculation unit 1080 calculates, as the difference value at the position of interest, the difference value between the gray level at the position of interest in the first converted image and the gray level at the corresponding position in the second converted image. However, if the noise reduction process is performed, the same process as in the first embodiment is performed.

Figure 5:
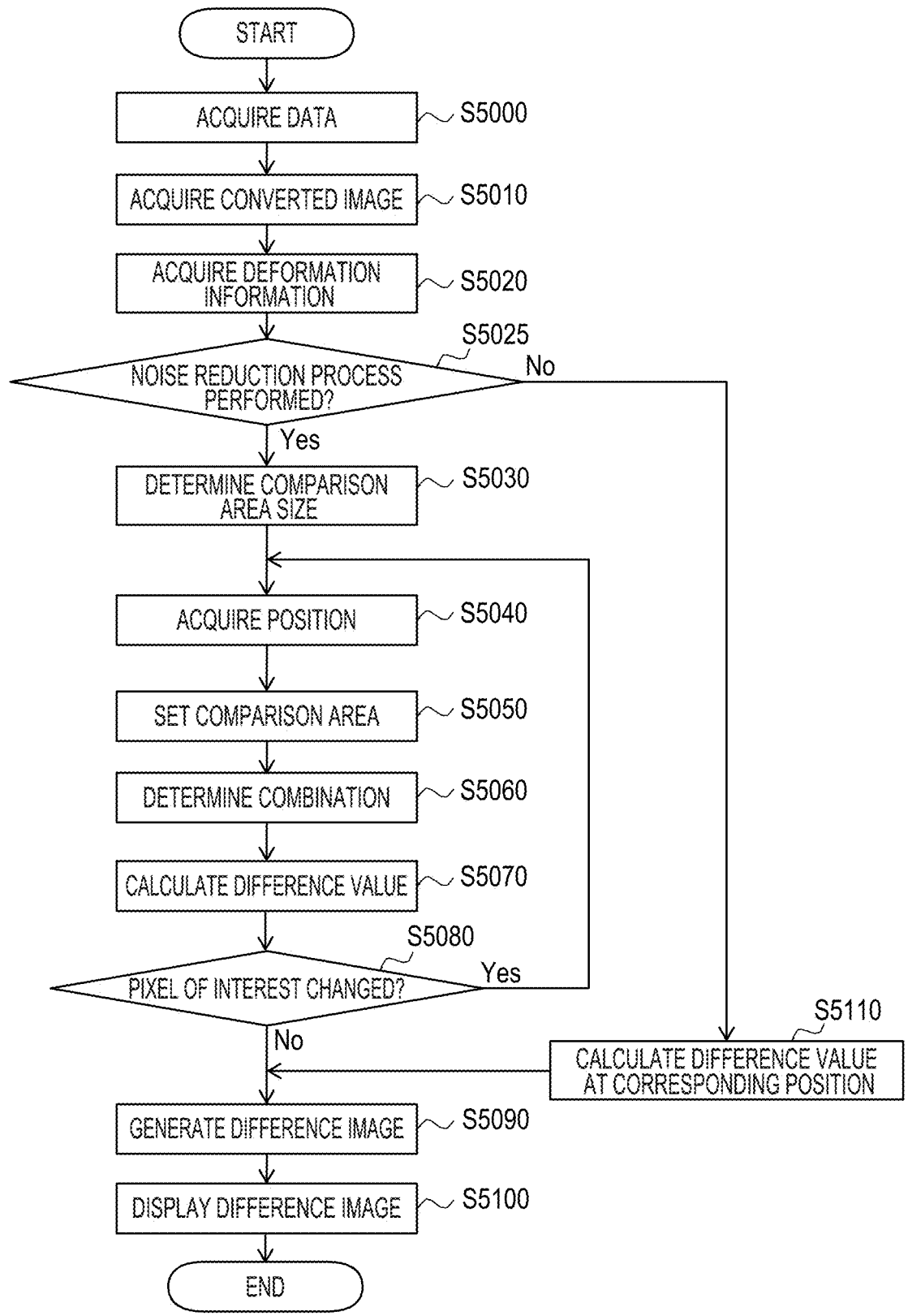
FIG. 5 is a flow diagram illustrating an example of the overall processing procedure according to a second embodiment.

FIG. 5 is a flowchart of the overall processing procedure performed by the image processing apparatus 100. Since the processes in steps S5000 to S5020 and steps S5030 to S5100 are the same as those in steps S2000 to S2020 and steps S2030 to S2100 of the first embodiment, respectively, description of the processes are not repeated. Only the difference from the flowchart illustrated in FIG. 2 is described below.

(S5025) (Noise Reduction Process Performed?)

In step S5025, the comparison area size determination unit 1040 determines whether to perform the noise reduction process on the basis of the pixel sizes of the first image and the second image.

In this case, if the pixel sizes of both the first image and second image are less than the predetermined threshold value, it is determined that the discretized position shift is small and, thus, noise reduction is not needed. The processing proceeds to step S5100. However, if the pixel sizes are greater than or equal to the predetermined threshold value, the processing proceeds to step S5030, where a noise reduction process similar to that of the first embodiment is performed. For example, as the threshold value, a value corresponding to the lesion size or the resolution of a modality or a value predetermined by the user is set.

According to the present embodiment, it is determined whether the noise reduction process is performed on the basis of the pixel size of each of the first image and the second image. However, the determination may be made on the basis of the sum of pixel sizes of the first and second images. Alternatively, different predetermined threshold values may be set for the x-, y-, and z-axis directions of the image. Still alternatively, the need for noise reduction may be determined for each of the axes, and it may be controlled whether the noise reduction process is performed for each of the axes. For example, if the pixel size in each of the x- and y-axis directions of the first image and the second image is less than the threshold value and the pixel size in the z-axis direction is greater than or equal to the threshold value, it is determined that noise reduction is not needed for the x-axis and y-axis directions, and, thus, the size of the comparison area may be set to 0. In addition, it is determined that noise reduction is needed for only z-axis direction and, thus, the size of the comparison area may be determined, as in the first embodiment. If it is determined that noise reduction is not needed for all three axis directions, the processing proceeds to step S5100. Otherwise, the processing proceeds to step S5030.

Note that in widely used CT images, the resolution (=the pixel size in the x and y directions) within a slice is often sufficient. For this reason, noise reduction may be always eliminated for the x and y directions without making a determination based on the pixel size. That is, it can be determined only whether noise reduction for the z direction is performed on the basis of the slice interval (=the pixel size in the z direction) of the input image. In this manner, determination can be made such that the noise reduction is not performed if the input image is based on a thin slice while the noise reduction is performed if the input image is based on a thick slice.

(S5110) (Calculation of Difference Value Between Corresponding Positions)

In step S5110, the difference calculation unit 1080 calculates the difference value between the gray levels at the corresponding positions in the first converted image and the second converted image (the second difference value in the first embodiment). At this time, as in step S5040, the corresponding positions in the images are acquired using the deformation information.

According to the present embodiment, by determining the need for a noise reduction process in accordance with the pixel size, unnecessary calculation can be eliminated if the pixel size of the input image is sufficiently small and, thus, the noise due to discretization is small. In addition, as compared with the first embodiment, over-erasure of the original difference values can be prevented.

Third Embodiment

An image processing apparatus according to the present embodiment is an apparatus that generates a three-dimensional difference image between a first image and a second image, as in the first embodiment. The image processing apparatus according to the present embodiment uses a deformed comparison area obtained by projecting a comparison area onto a deformed image subjected to deformation registration so that the same parts in the images are registered to each other and generating a noise-reduced three-dimensional difference image. As in the first embodiment, the image processing apparatus according to the present embodiment acquires the first converted image and the second converted image converted from the first image and the second image, respectively, so that each image has a different resolution from the original image. Thereafter, the image processing apparatus sets a comparison area around the corresponding position in the second converted image, which corresponds to the position of interest in the first converted image. Subsequently, by using the deformation information, the image processing apparatus projects the comparison area onto a second deformation transformation image acquired by deformation-registering the second converted image so that the gray value of each of the pixels of the second converted image is similar to that of the first converted image. Subsequently, on the basis of the gray level at the position of interest in the first converted image and the gray levels of the plurality of pixels in the deformed comparison area set around the corresponding position on the second deformation transformation image, the image processing apparatus calculates the difference at the position of interest and generates a three-dimensional difference image having the calculated value as the gray level at the position of interest therein. In this manner, a deformed image of the second image and the difference image can be acquired in which the same part as in the first image is located at the same position as in the first image. Accordingly, by displaying these images side by side, the user can easily check at which positions in the first image and the deformed image the gray levels used to calculate the difference value in the difference image are picked up. The configuration and processing according to the present embodiment are described below with reference to FIGS. 6 and 7.

Figure 6:
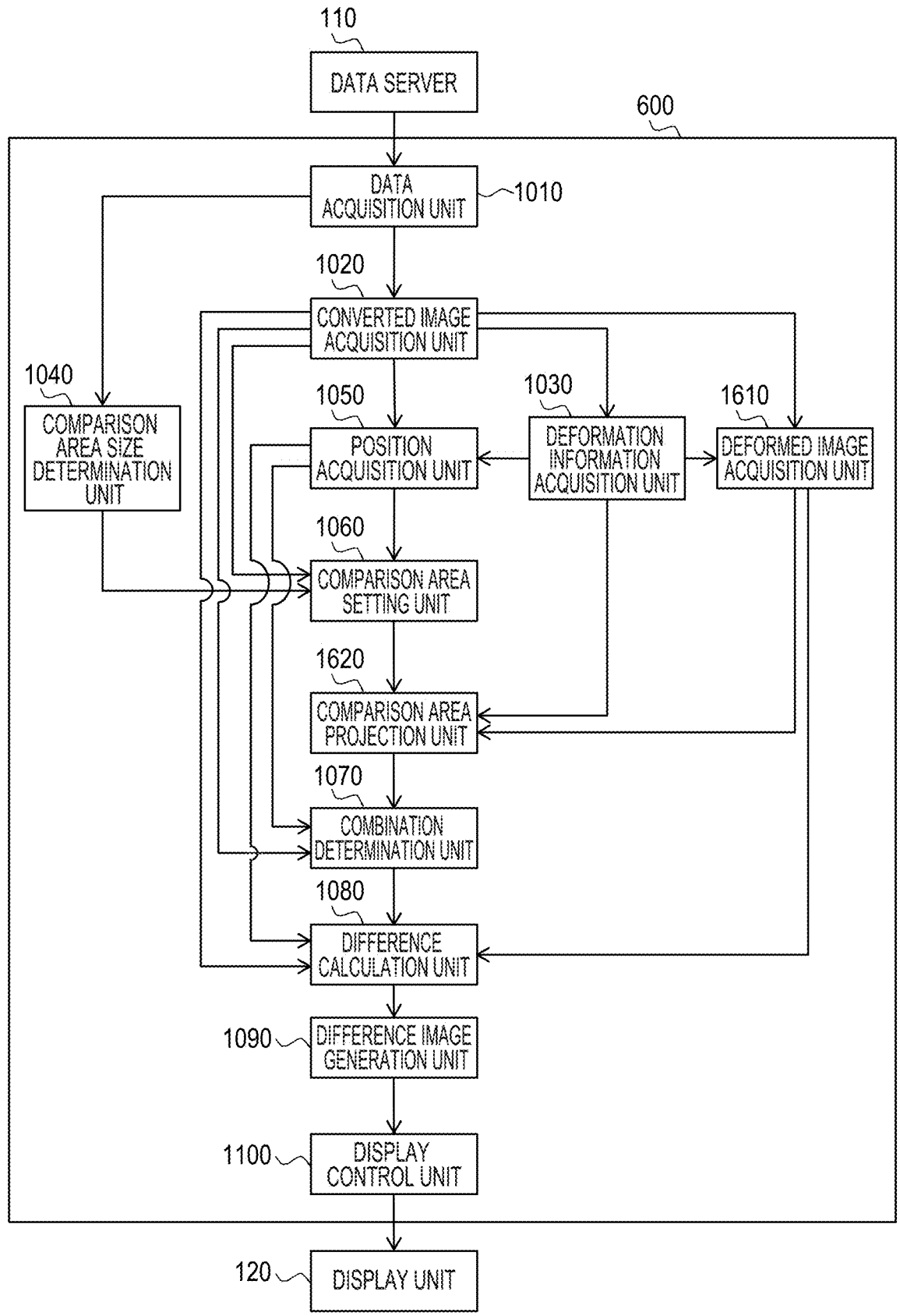
FIG. 6 is a diagram illustrating an example of the device configuration of an image processing apparatus according to a third embodiment.

FIG. 6 illustrates the configuration of a diagnostic imaging system according to the present embodiment. Because the data server 110 and the display unit 120 are the same as those in the first embodiment, description thereof is not repeated. An image processing apparatus 600 is composed of the constituent elements described below. A data acquisition unit 1010, a converted image acquisition unit 1020, a deformation information acquisition unit 1030, a comparison area size determination unit 1040, a position acquisition unit 1050, a comparison area setting unit 1060, a difference image generation unit 1090, and a display control unit 1100 have functions the same as those according to the first embodiment. Accordingly, the description of the constituent elements is not repeated.

Figure 7:
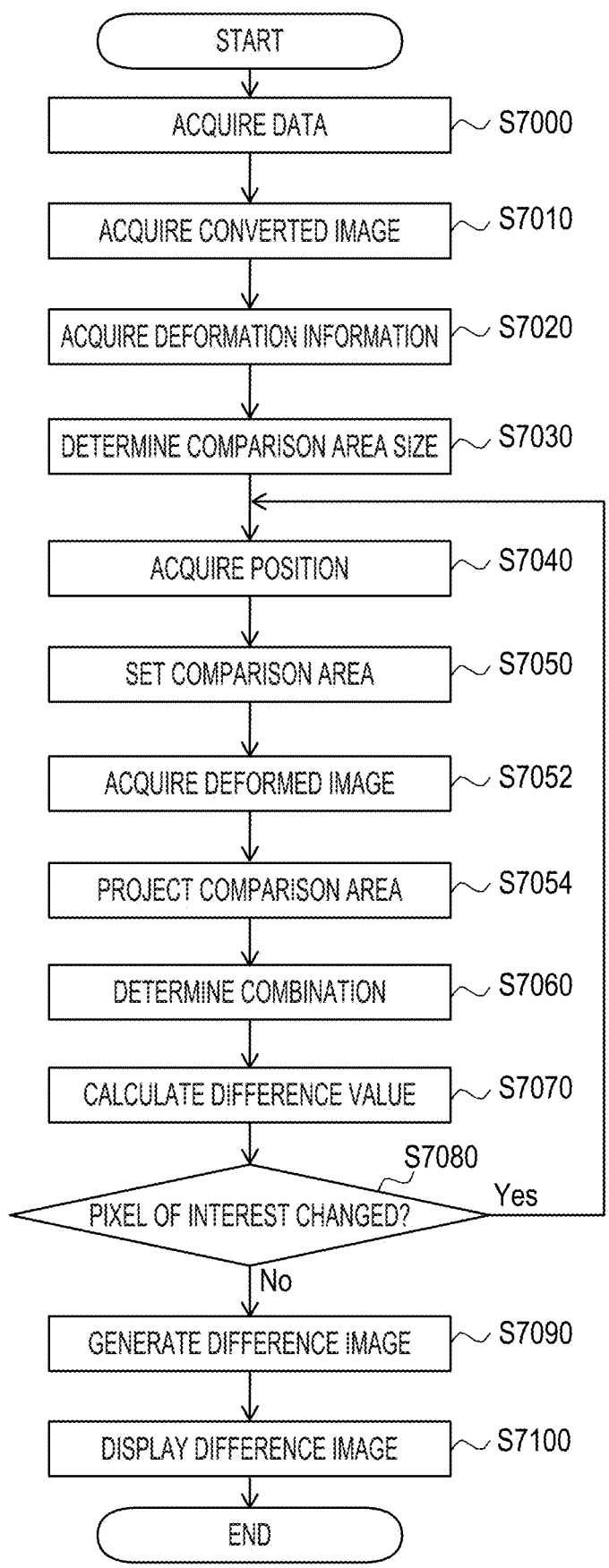
FIG. 7 is a flow diagram illustrating an example of the overall processing procedure according to the third embodiment.

By using the deformation information acquired by the deformation information acquisition unit 1030, a deformed image acquisition unit 1610 acquires a second deformation transformation image obtained by deforming the second converted image. A comparison area projection unit 1620 uses the deformation information acquired by the deformation information acquisition unit 1030 to project the comparison area set in the second converted image by the comparison area setting unit 1060 onto the second deformation transformation image and obtains the deformed comparison area. The combination determination unit 1070 determines a combination of the gray level at the position of interest in the first converted image and the gray levels at a plurality of positions in the comparison area of the second converted image as the target of the comparison process (calculation of the difference). The difference calculation unit 1080 calculates the gray level at the position of interest on the basis of the combination of grey levels determined by the combination determination unit 1070, that is, the gray level of the pixel of interest in the first converted image and the gray levels of the plurality of pixels in the comparison area of the second converted image. FIG. 7 is a flowchart of the overall processing procedure performed by the image processing apparatus 600. In steps S7000 to S7050 and steps S7080 to S7100, the same processes are performed as in steps S2000 to S2050 and steps S2080 to 2100 of the first embodiment, respectively. Accordingly, the description of the steps are not repeated. Hereinafter, only the difference from the flowchart illustrated in FIG. 2 is described.

(S7052) (Acquisition of Deformed Image)

In step S7052, by using the deformation information acquired in step S7020, the deformed image acquisition unit 1610 acquires a second deformation transformation image obtained by deforming the second converted image. Thereafter, the deformed image acquisition unit 1610 outputs the acquired second deformation transformation image to a comparison area projection unit 1720 and the difference calculation unit 1080.

(S7054) (Projection of Comparison Area)

In step S7054, the comparison area projection unit 1620 projects the comparison area set in the second converted image in step S7050 onto the second deformation transformation image by using the deformation information acquired in step S7020 to obtain a deformed comparison area. Thereafter, the comparison area projection unit 1620 outputs information about the deformed comparison area to the difference calculation unit 1080.

Note that the comparison area of the second converted image to be projected may be the entire comparison area or a plurality of positions sampled from within the comparison area. If the entire comparison area is projected, the entire area within the contour of the comparison area projected onto the second deformation transformation image by using the deformation information can be the deformed comparison area.

(S7060) (Determination of Combination)

In step S7060, the combination determination unit 1070 determines a combination of gray levels to be subjected to a comparison process (calculation of a difference). The combination determination unit 1070 first interpolates the gray level at the position of interest in the first converted image and the gray levels of the pixels in the comparison area of the second converted image, which are acquired in step S7040. Note that an existing image processing technique can be used for the interpolation of the gray levels. For example, nearest neighbor interpolation, linear interpolation, or cubic interpolation can be used. Note the interpolation of the gray level of the pixels in the comparison area of the second converted image is not always needed. The combination determination unit 1070 may determine the combination of gray levels so that the difference between the gray level at the position of interest in the first converted image and each of the gray levels of all the pixels in the comparison area of the second converted image are calculated. Furthermore, the combination determination unit 1070 may sample at least one pixel from among the pixels included in the comparison area and determine a combination of the gray level of the pixel and the gray level at the position of interest as the combination to be subjected to difference calculation. For example, the combination determination unit 1070 samples the maximum gray level and the minimum gray level from among the pixels included in the comparison area. Thereafter, the combination determination unit 1070 determines, as the combinations subjected to difference calculation, the combination of the maximum gray level included in the comparison area and the gray level at the position of interest and the combination of the minimum gray level included in the comparison area and the gray level at the position of interest. Note that the gray levels to be sampled are not limited to the maximum and minimum values. Three or more values may be sampled, or one value, such as the maximum gray level or the minimum gray level, may be sampled. Alternatively, the combination determination unit 1070 may acquire a gray level range having the maximum gray level and the minimum gray level at both ends (the upper limit value and the lower limit value) in the comparison area and acquire the gray level at the position of interest and the gray level range in the comparison area as the combination to be subjected to difference calculation. Note that the gray level range in the comparison area may be other than the maximum and minimum gray levels. For example, the gray level range may be the maximum value and the minimum value after the outlier of the gray level is removed.

The combination determination unit 1070 outputs, to the difference calculation unit 1080, information indicating the determined combination of the gray levels to be subjected to difference calculation. The information indicating the combination of the gray levels output from the combination determination unit 1070 may be information indicating all the combinations of the gray level at the position of interest in the first converted image and the gray level of each of the pixels in the comparison area of the second converted image. Alternatively, the combination determination unit 1070 may output only the information indicating the combination of the gray level of a pixel sampled from among the pixels included in the comparison area and the gray level at the position of interest.

(S7070) (Calculation of Difference Value)

In step S7070, the difference calculation unit 1080 obtains the difference value provided to a difference image on the basis of the combination of the gray level at the position of interest in the first converted image acquired in step S7060 and the gray level in the deformed comparison area of the second deformation transformation image projected in step S7054. The difference from the process in step S2060 according to the first embodiment is only that the second converted image is changed to the second deformation transformation image, and the comparison area is changed to the deformed comparison area. The other processes remain unchanged.

As described above, the processing is performed by the image processing apparatus 600.

According to the present embodiment, the following effect is provided. That is, a user can observe a part in the deformed image of the second image, in which the position of the part is substantially the same as in the first image, and the same part in the noise-reduced difference image while easily comparing the parts. As a result, the user can easily determine whether the difference value in the difference image represents the difference caused by a lesion, as compared with the first embodiment.

(Modification 3-1) (Image Similarity is Calculated in Consideration of Discretization Position Shift)

As in Modification 1-1 of the first embodiment, when the image similarity is calculated, the image similarity may be obtained on the basis of the difference value in which noise caused by a discretization position shift is reduced. The modification uses the minimum value of the difference between the gray level at the position of interest in the first converted image and each of the gray levels in the deformed comparison area of the second deformation transformation image. In this manner, the image similarity can be obtained in consideration of a discretized position shift. As a result, the difference image with further reduced noise can be obtained.

Fourth Embodiment

As in the first embodiment, the image processing apparatus according to the present embodiment is an apparatus that generates a difference image between three-dimensional images. The image processing apparatus according to the present embodiment sets a comparison area at each of the position of interest of the first converted image and the corresponding position in the second converted image and obtains the difference value on the basis of the gray levels in each of the comparison areas. Note that as in the first embodiment, the direction in which the comparison area is set in the second converted image and the difference from the position of interest in the first converted image is obtained is defined as a forward direction. In addition, the direction in which the comparison area is set in the first converted image and the difference from the corresponding position in the second converted image is obtained is defined as a reverse direction. The image processing apparatus according to the present embodiment obtains a difference value in each of the forward direction and the reverse direction at the position of interest in the difference image and, thereafter, a representative difference value obtained by integrating the two difference values is used as the gray level of the difference image to be generated. In this manner, a signal that cannot be obtained from calculation for only one direction can be left in the difference image. The configuration and processing according to the present embodiment are described below with reference to FIGS. 1 and 8.

The configuration of the image processing apparatus according to the present embodiment is the same as that according to the first embodiment. However, the functions of the comparison area setting unit 1060, the combination determination unit 1070, and the difference calculation unit 1080 differ from those of the first embodiment and, thus, the functions are described below. The other configurations have the same functions as those of the first embodiment and, thus, the description of the configurations is not repeated.

The comparison area setting unit 1060 sets a comparison area having the size of the comparison area around each of the position of interest in the first converted image and the corresponding position in the second converted image. The combination determination unit 1070 determines a combination of the gray level at the position of interest in the first converted image and the gray levels at a plurality of positions in the comparison area of the second converted image as the target of the comparison process (calculation of the difference). The difference calculation unit 1080 calculates a difference value in the forward direction and a difference value in the reverse direction on the basis of the combination of gray levels determined by the combination determination unit 1070 and obtains a representative difference value by integrating the two difference values.

Figure 8:
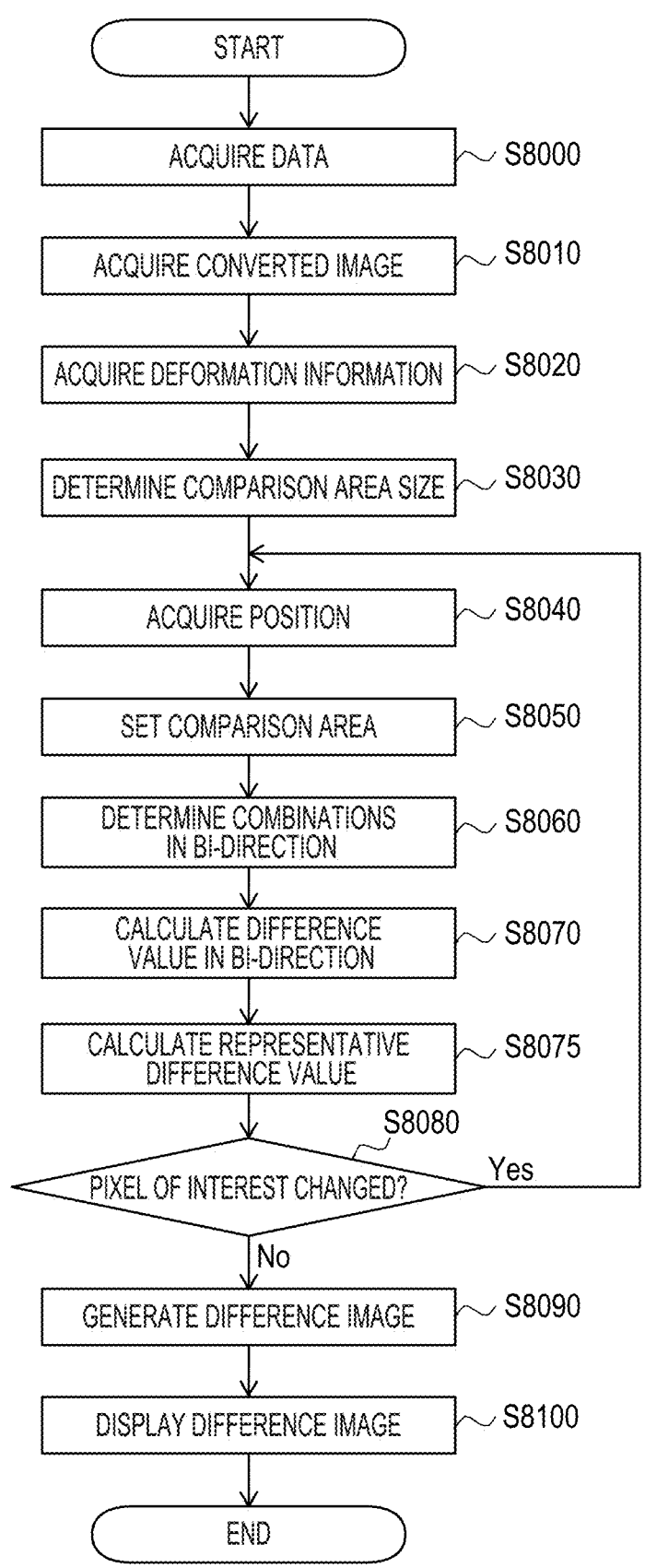
FIG. 8 is a flow diagram illustrating an example of the overall processing procedure according to a fourth embodiment.

FIG. 8 is a flowchart of the overall processing procedure performed by the image processing apparatus 100. Since the processes in steps S8000 to S8040 and steps S8080 to S8100 are the same as those in steps S2000 to S2040 and steps S2080 to S2100 of the first embodiment, respectively, description of the processes is not repeated. Only the difference from the flowchart illustrated in FIG. 2 is described below.

(S8050) (Setting of Comparison Area)

In step S8050, the comparison area setting unit 1060 sets a first comparison area having the size of the comparison area determined in step S8030 around the position of interest in the first converted image. In addition, as in step S2050 according to the first embodiment, the comparison area setting unit 1060 sets a second comparison area having the size of the comparison area determined in step S8030 around the corresponding position in the second converted image. Thereafter, the comparison area setting unit 1060 outputs the information regarding the set first comparison area and second comparison area to the combination determination unit 1070.

(S8060) (Determination of Combinations in Bi-Direction)

In step S8060, the combination determination unit 1070 interpolates the gray level at the position of interest in the first converted image acquired in step S8040 and the gray level of the pixel in the comparison area of the second converted image and determines a combination (in the forward direction). In addition, the combination determination unit 1070 interpolates the gray level at the corresponding position in the second converted image and the gray level of each of the pixels in the first comparison area of the first converted image and determines a combination (in the reverse direction). This process is obtained by merely exchanging the position of interest for the corresponding position in the process in step S2060 of the first embodiment and can be performed in the same manner as in step S2060. Note that the variety of methods described in step S2060 can be used to determine the combination.

(S8070) (Calculation of Difference Values in Bi-Direction)

As in step S2070 according to the first embodiment, in step S8070, the difference calculation unit 1080 calculates the difference value (in the forward direction) at the position of interest on the basis of the combination of the gray level at the position of interest in the first converted image and each of the pixels in the second comparison area of the second converted image. In addition, the difference calculation unit 1080 calculates the difference value (in the reverse direction) at the position of interest on the basis of the gray level at the corresponding position in the second converted image and the gray level of each of the pixels in the first comparison area of the first converted image. This process is obtained by merely exchanging the position of interest for the corresponding position in the process in step S2070 of the first embodiment and can be performed in the same manner as in step S2070. Note that the variety of methods described in step S2070 can be used to determine the difference value.

(S8075) (Calculation of Representative Difference Value)

In step S8075, the difference calculation unit 1080 integrates the difference value in the forward direction and the difference value in the reverse direction calculated in step S8070 to obtain the representative difference value. For example, the difference calculation unit 1080 compares the absolute values of the two difference values with each other and obtains the larger one as the representative difference value. Thereafter, the difference calculation unit 1080 outputs the obtained representative difference value to the difference image generation unit 1090 as the gray level of the difference image at the position of interest.

In some cases, for a signal of a small-sized lesion that exists only in one of the first image and the second image, the difference value is obtained in one of the forward direction and the reverse direction while the difference value is not obtained in the other direction. Although the signal may disappear when the difference value in only one direction is used, the difference value can remain in the difference image if the representative difference value is calculated using the difference values in bi-direction.

According to the present embodiment, the difference value having the larger absolute value is defined as the representative difference value. However, the difference value having the smaller absolute value may be defined as the representative difference value. Alternatively, the average value of the difference value in the forward direction and the difference value in the reverse direction may be defined as the representative difference value. In this manner, the difference value from a signal existing only in one image is reduced, while the noise signal can be reduced more.

According to the present embodiment, the size of the comparison area need not always be adaptively determined on the basis of the pixel size of the input image. That is, the size of the comparison area suitable for a typical pixel size may be set in advance as a default value and be used. In this case, the comparison area size determination unit 1040 and the process of step S8030 are not needed.

According to the present embodiment, the following effect is provided. That is, the risk of a signal that exists in only one image, such as a signal representing a small lesion, being erased or a risk of a lesion being displayed smaller than the original size of the lesion can be reduced, as compared with the first embodiment.

Fifth Embodiment

An image processing apparatus according to the present embodiment is an apparatus that generates a three-dimensional difference image between a plurality of three-dimensional images (a first image and a second image), as in the first embodiment. According to the present embodiment, an example of implementing the present invention with a simpler configuration is described. The configuration and processing according to the present embodiment are described below with reference to FIGS. 9 and 10.

Figure 9:
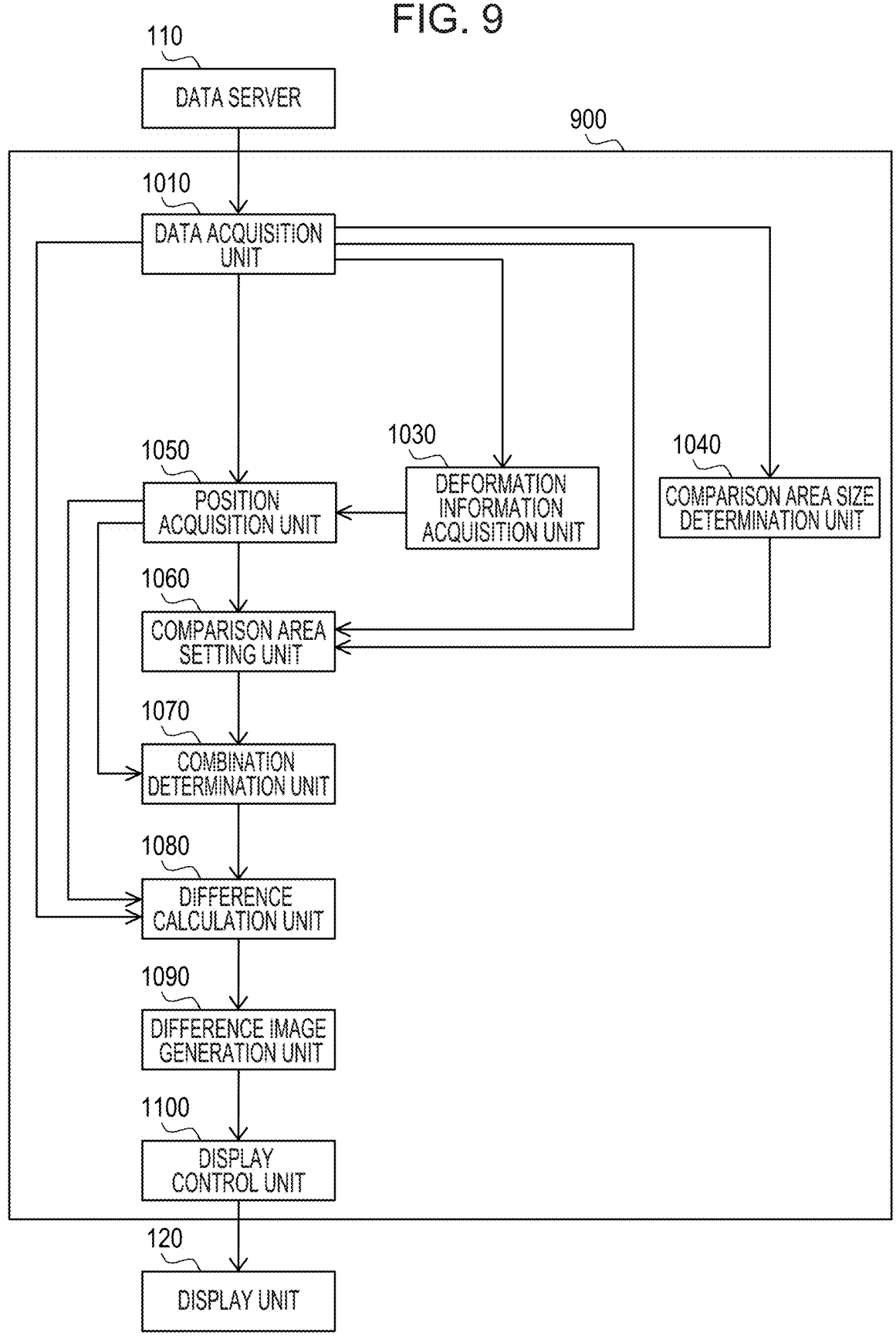
FIG. 9 is a diagram illustrating the device configuration of an image processing apparatus according to a fifth embodiment.

FIG. 9 illustrates the configuration of a diagnostic imaging system according to the present embodiment. A data server 110 and a display unit 120 have the same functions as those in the first embodiment and, thus, descriptions of the data server 110 and the display unit 120 are not repeated.

An image processing apparatus 900 is composed of the following constituent elements. Since a data acquisition unit 1010, a comparison area size determination unit 1040, a difference image generation unit 1090, and a display control unit 1100 have the same functions as those in the first embodiment, the description of the constituent elements is not repeated. The other configurations are described below.

The deformation information acquisition unit 1030 acquires the deformation information indicating the correspondence relationship between the positions in the first image and the second image. The position acquisition unit 1050 acquires a position of interest in the first image and acquires the corresponding position in the second image, which corresponds to the position of interest in the first image, by using the deformation information acquired by the deformation information acquisition unit 1030. The comparison area setting unit 1060 sets a comparison area having the size of the comparison area around the corresponding position in the second image. The combination determination unit 1070 determines, as a target of a comparison process (calculation of the difference), a combination of the gray level at the position of interest in the first converted image and the gray levels at a plurality of positions in the comparison area of the second converted image. The difference calculation unit 1080 calculates the difference value at the position of interest on the basis of the combination determined by the combination determination unit 1070, that is, the gray level of the pixel of interest in the first converted image and the gray levels of a plurality of pixels in the comparison area of the second converted image.

Figure 10:
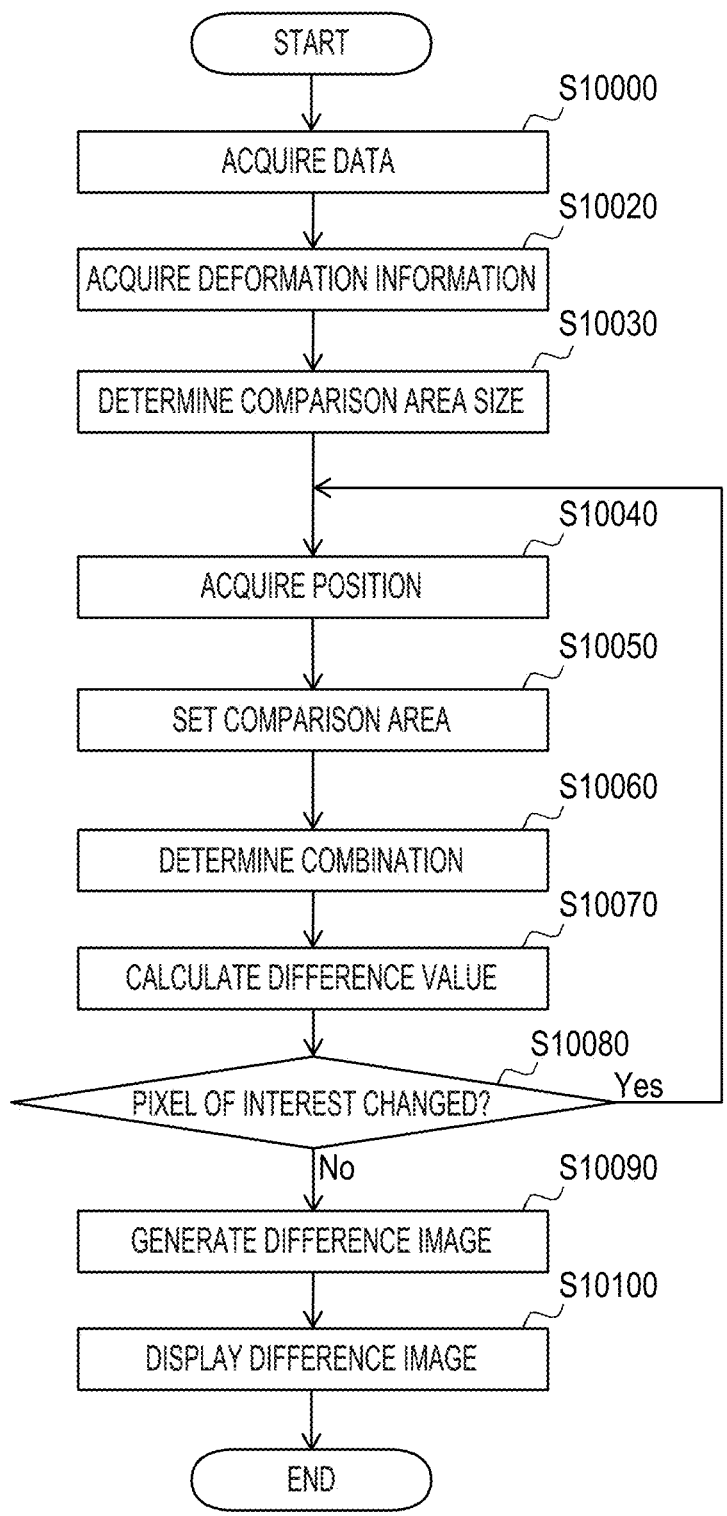
FIG. 10 is a flow diagram illustrating an example of the overall processing procedure according to the fifth embodiment.

FIG. 10 is a flowchart of the overall processing procedure performed by the image processing apparatus 900. Because the process performed in step S10100 is the same as in step S2100 according to the first embodiment, description of the process is not repeated. Only the difference from the flowchart illustrated in FIG. 2 is described below.

(S10000) (Acquisition of Data)

In step S10000, the data acquisition unit 1010 acquires a first image and a second image input to the image processing apparatus 900. Thereafter, the data acquisition unit 1010 outputs the acquired first image and second image to the deformation information acquisition unit 1030, the position acquisition unit 1050, the comparison area setting unit 1060, the combination determination unit 1070, and the difference calculation unit 1080. In addition, the data acquisition unit 1010 outputs the information regarding the pixel sizes of the first image and the second image to the comparison area size determination unit 1040.

(S10020) (Acquisition of Deformation Information)

In step S10020, the deformation information acquisition unit 1030 acquires deformation information such that the pixels representing the same part in the first image and the second image substantially match. That is, the deformation information acquisition unit 1030 performs a registration process (a deformation estimation process) between the first image and the second image. Thereafter, the deformation information acquisition unit 1030 outputs the acquired deformation information to the position acquisition unit 1050.

According to the present embodiment, the deformation information can be obtained by an existing image processing technique as in the first embodiment.

(S10030) (Determination of Comparison Area Size)

In step S10030, the comparison area size determination unit 1040 determines the size of the comparison area used to calculate the difference value on the basis of the pixel size of the first image and the pixel size of the second image. Thereafter, the comparison area size determination unit 1040 outputs the determined size of the comparison area to the comparison area setting unit 1060.

According to the present embodiment, as in the first embodiment, the following characteristic is used. That is, due to a shift of the discretized position between a first image and a second image during image generation, the position of the pixel at which the original imaging signal of an object is most reflected is shifted between the first converted image and the second converted image by up to the sum of the half pixel sizes of the pixels of the original images. That is, the sum of the half pixel sizes of the first image and the second image is selected as the size of the comparison area.

(S10040) (Acquisition of Position)

In step S10040, the position acquisition unit 1050 acquires the position of interest (the pixel of interest) in the first image and acquires the corresponding position in the second image, which corresponds to the position of interest, by using the deformation information acquired in step S10020. Thereafter, the position acquisition unit 1050 outputs the acquired position to the comparison area setting unit 1060, the combination determination unit 1070, and the difference calculation unit 1080.

(S10050) (Setting of Comparison Area)

In step S10050, the comparison area setting unit 1060 sets a comparison area having the size of the comparison area determined in step S10030 around the corresponding position in the second image. Thereafter, the comparison area setting unit 1060 outputs the information regarding the set comparison area to the combination determination unit 1070.

(S10060) (Determination of Combination)

In step S10060, the combination determination unit 1070 determines a combination of gray levels to be subjected to a comparison process (calculation of the difference). The combination determination unit 1070 first interpolates the gray level at the position of interest in the first converted image and the gray level of the pixel in the comparison area of the second converted image, which are acquired in step S10040. Note that an existing image processing technique can be used for the interpolation of the gray level. For example, nearest neighbor interpolation, linear interpolation, or cubic interpolation can be used. Also note that interpolation of the gray levels of the pixels in the comparison area of the second converted image is not always needed. The combination determination unit 1070 may determine the combination of gray levels so that the difference are calculated between the gray level at the position of interest in the first converted image and each of the gray levels of all the pixels in the comparison area of the second converted image. Alternatively, the combination determination unit 1070 may sample at least one pixel from among the pixels included in the comparison area and determine a combination of the gray level of the pixel and the gray level at the position of interest as the combination to be subjected to difference calculation. For example, the combination determination unit 1070 samples the maximum gray level and the minimum gray level from among the pixels included in the comparison area. Thereafter, the combination determination unit 1070 determines, as the combinations subjected to difference calculation, the combination of the maximum gray level included in the comparison area and the gray level at the position of interest and the combination of the minimum gray level included in the comparison area and the gray level at the position of interest. Note that the gray levels to be sampled are not limited to the maximum and minimum values. Three or more values may be sampled, or one value, such as the maximum gray level or the minimum gray level, may be sampled. Alternatively, the combination determination unit 1070 may acquire a gray level range having the maximum gray level and the minimum gray level in the comparison area at both ends (the upper limit value and the lower limit value) and acquire the gray level at the position of interest and the gray level range in the comparison area as the combination to be subjected to difference calculation. Note that the gray level range in the comparison area may be other than the maximum and minimum gray levels. For example, the gray level range may be the maximum value and the minimum value after the outlier of the gray level is removed.

(S10070) (Calculation of Difference Value)

In step S10070, the difference calculation unit 1080 acquires the difference value provided to the difference image on the basis of the combination of the gray level at the position of interest in the first image and the gray levels of the plurality of positions in the comparison area of the second image determined in step S10060. Thereafter, the difference calculation unit 1080 outputs the difference value to the difference image generation unit 1090.

According to the first embodiment, the difference value is calculated from the gray levels of the reference image (the first image or first converted image) and the second converted image. However, according to the present embodiment, the difference value is calculated from the gray levels in the first image and the second image in the same manner as in step S2070 according to the first embodiment. That is, the difference is calculated between the gray level at the position of interest in the first image and the gray level at each of the plurality of positions in the comparison area of the second image, and the minimum value of the differences is acquired as a difference value provided to the difference image. Note that when the gray level is acquired from each of the plurality of positions in the comparison area of the second image, the positions of all the pixels in the comparison area may be considered as the above-described plurality of positions, and the gray level may be acquired from each of the pixels. Alternatively, as the above-described plurality of positions in the comparison area, measurement points may be set in the comparison area at predetermined intervals which are smaller than the pixel pitch, and the gray level at each of the measurement points is acquired through interpolation using the gray levels of the neighboring pixels.

(S10080) (Change Position of Interest?)

In step S10080, the position acquisition unit 1050 determines whether the difference values at all of the positions (all pixels) in the first image have been calculated. If the difference values at all of the positions have been calculated, the processing proceeds to step S10090. However, if the difference values at all of the positions have not been acquired, the processing returns to step S10040.

Note that according to the present embodiment, the difference value may be calculated not for all of the positions in the first image, but for some of the positions in the first image extracted by an existing image processing technique in advance. As a result, the processing time required for noise reduction can be reduced.

(S10090) (Generation of Difference Image)

In step S10090, the difference image generation unit 1090 generates a difference image (a first difference image) having gray levels each equal to the difference value at one of the positions (pixels) in the first image. Thereafter, the difference image generation unit 1090 stores the obtained difference image in the data server 110. In addition, the difference image generation unit 1090 outputs the obtained difference image to the display control unit 1100. Note that at the same time, the difference image generation unit 1090 may generate a widely used difference image (a second difference image) having gray levels each equal to the second difference value (the difference between the gray level at a position of interest in the first image and the gray level at the corresponding position in the second image) calculated in step S10070.

As described above, the processing is performed by the image processing apparatus 900.

As described above, the same effect as that according to the first embodiment can be obtained without acquiring the first converted image and the second converted image. That is, by calculating the difference value from the comparison area of the minimum necessary size in consideration of the discretized position shift, the user can observe a difference image having the necessary signal remaining therein and reduced noise generated by the difference in gray level caused by a shift of the discretized position between the images. Note that like the present embodiment, each of the second to fourth embodiments can be implemented without acquiring the first converted image and the second converted image.

Sixth Embodiment

An image processing apparatus according to the present embodiment is an apparatus that generates a three-dimensional difference image between the first image and the second image, as in the first embodiment. However, the image processing apparatus according to the present embodiment generates a difference image in which noise caused by a difference in gray level between images caused by the difference in pixel size is reduced when the pixel sizes are different in the images. The image processing apparatus according to the present embodiment is described below.

In general, to convert continuous signal data obtained from an object into gray levels of discretized pixels and reconstruct an image (such as a CT image), a weighted average value of the signal data in a predetermined zone (for example, the pixel size in a plane of a slice image or the slice thickness) is used. That is, the gray level of a pixel having a large pixel size is calculated by smoothing a wide range of signal data, as compared with a pixel having a small pixel size. In the image processing apparatus according to the present embodiment, if the pixel size of the second image is smaller than that of the first image, the gray level of the second image is approximately regarded as the signal data. Thereafter, the image processing apparatus according to the present embodiment smoothens the gray level of the pixel in an area of the second image having the same size as that of a pixel of the first image and, thus, approximately obtains the gray level generated from the signal data in an area having a size the same as that of a pixel of the first image. In this manner, the image processing apparatus generates a second smoothed image which is a second image subjected to a smoothing process. Subsequently, the generated second smoothed image is used instead of the second image, and a process of generating a difference image is performed in a similar manner to that of the first embodiment. In this way, a smoothing area of the second image is selected in which the difference between the gray level and the gray level at the pixel of interest in the first image is the smallest. As a result, a change in gray level caused by a slight shift of the smoothing area can be absorbed. In contrast, if the pixel size of the first image is smaller than that of the second image, a first smoothed image obtained by smoothing the first image is used instead of the first image in the same manner, and a process of generating a difference image similar to that of the first embodiment is performed. In this manner, in the case of inputting two images having different pixel sizes, the user can observe a difference image with less noise than in the first embodiment. The configuration and processing according to the present embodiment are described below with reference to FIGS. 11 and 12.

Figure 11:
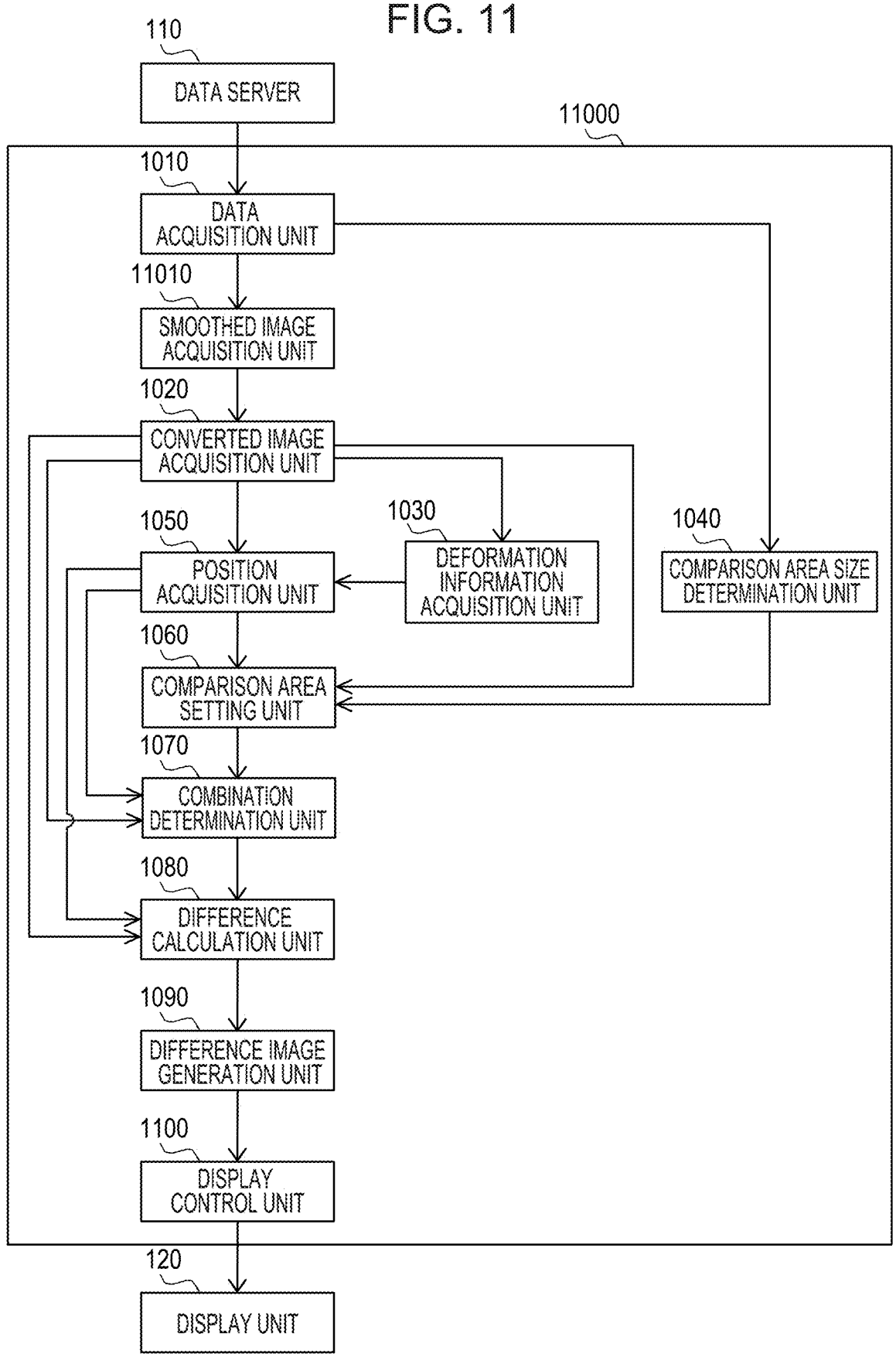
FIG. 11 is a diagram illustrating an example of the device configuration of an image processing apparatus according to a sixth embodiment.

FIG. 11 illustrates the configuration of the diagnostic imaging system according to the present embodiment. The function of a smoothed image acquisition unit 11010 is described below. The other configurations have the same functions as those of the first embodiment and, thus, description of the functions is not repeated.

The smoothed image acquisition unit 11010 determines which one of the pixel size of the first image and the pixel size of the second image acquired from the data acquisition unit 1010 is larger. If the pixel size of the second image is smaller than the pixel size of the first image, the smoothed image acquisition unit 11010 acquires the second smoothed image obtained by smoothing the second image. However, if the pixel size of the first image is smaller than the pixel size of the second image, the smoothed image acquisition unit 11010 acquires the first smoothed image obtained by smoothing the first image.

Figure 12:
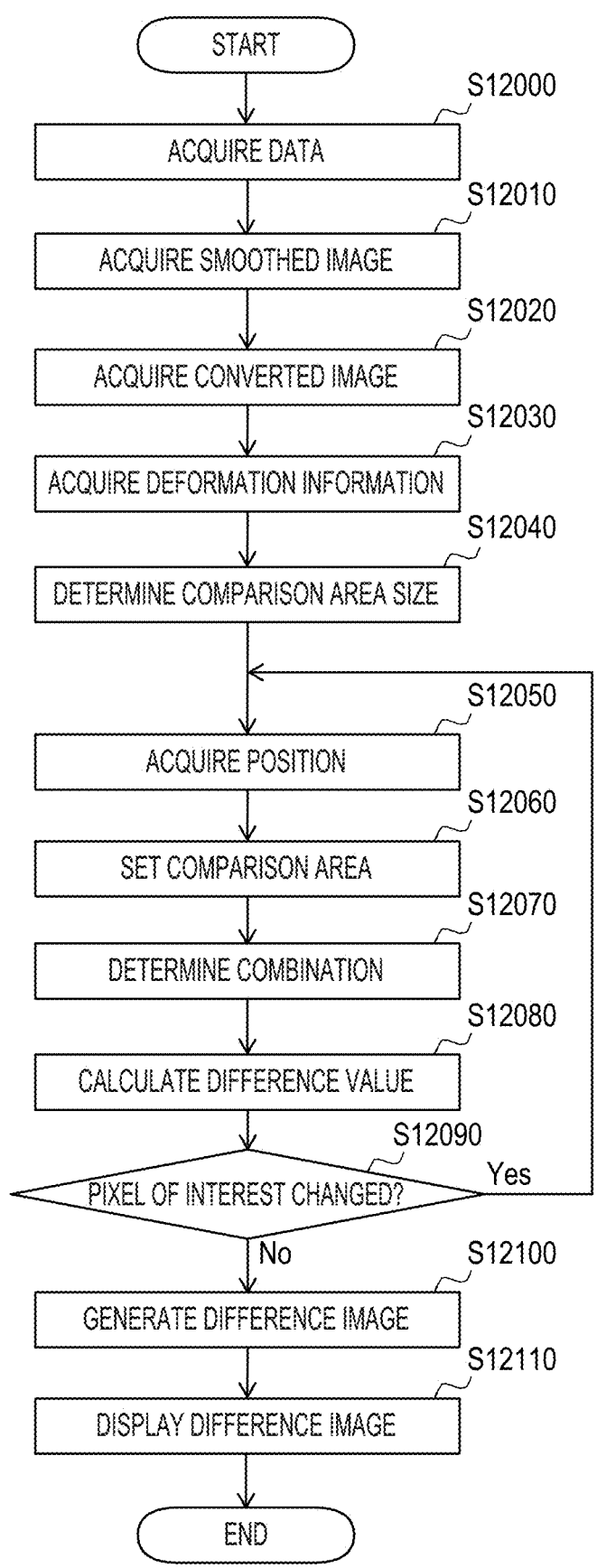
FIG. 12 is a flow diagram illustrating an example of the overall processing procedure according to the sixth embodiment.

FIG. 12 is a flowchart of the overall processing procedure performed by an image processing apparatus 11000. Since the processes performed in steps S12030 to S12110 are the same as those performed in steps S2020 to S2100 of the first embodiment, respectively, description of steps S12030 to S12110 is not repeated. Only the difference from the flowchart illustrated in FIG. 2 is described below.

(S12000) (Data Acquisition)

In step S12000, the data acquisition unit 1010 acquires the first image, the second image, and the pixel size of each of the images input to the image processing apparatus 11000. Thereafter, the data acquisition unit 1010 outputs the acquired first image, second image, and pixel size of each of the images to the smoothed image acquisition unit 11010. In addition, the data acquisition unit 1010 outputs the information regarding the pixel sizes of the first and second image to the comparison area size determination unit 1040.

(S12010) (Acquisition of Smoothed Image)

In step S12010, the smoothed image acquisition unit 11010 determines which one of the pixel size of the first image and the pixel size of the second image acquired from the data acquisition unit 1010 is larger. If the first image has a first pixel size which is a larger one of the two pixel sizes (if the pixel size of the second image is smaller than the pixel size of the first image), the smoothed image acquisition unit 11010 smoothens the second image to acquire the second smoothed image. Thereafter, the smoothed image acquisition unit 11010 outputs the acquired second smoothed image and first image to the converted image acquisition unit 1020. In this case, the image processing apparatus 11000 replaces the second smoothed image with the second image and performs the subsequent processing. However, if the first image has a second pixel size which is a smaller one of the two pixel sizes, the smoothed image acquisition unit 11010 acquires the first smoothed image obtained by smoothing the first image. Thereafter, the smoothed image acquisition unit 11010 outputs the acquired first smoothed image and the second image to the converted image acquisition unit 1020. In this case, the image processing apparatus 11000 replaces the first smoothed image with the first image and performs the subsequent processing. Note that since the smoothed image acquisition unit 11010 has already acquired the pixel size of each of the images from the data acquisition unit 1010, the smoothed image acquisition unit 11010 can perform the above-described processing.

More specifically, an example in which the first image has the first pixel size is described. According to the present embodiment, to perform, on the second image having the smaller pixel size, a process approximate to the process performed when the first image having the larger pixel size is reconstructed from signal data, the smoothed image acquisition unit 11010 smoothens the second image by using a kernel having the same size as the pixel size of the first image. For example, assume that the pixel sizes of the first image in the x-, y-, and z-axis directions are 1.5 mm, 1.5 mm, and 5 mm, respectively, and the pixel sizes of the second image in the x-, y-, and z-axis directions are 0.5 mm, 0.5 mm, and 1 mm, respectively. At this time, the kernel size is 1.5 mm×1.5 mm×5 mm, which is the size corresponding to 3×3×5 pixels in the second image. An existing smoothing process is performed using this kernel. As the smoothing process, a process of evenly averaging the gray levels of 3×3×5 pixels may be performed, or a process of calculating a weighted average, such as the smoothing process using a Gaussian filter, may be performed. Note that, in widely used CT images, the resolution (=pixel size in the x- and y-directions) in a slice is mostly sufficiently high and, therefore, a configuration that does not perform noise reduction in the x- and y-directions may be employed. In this case, the kernel size in the x- and y-axis directions can be set to 1 pixel, and only the gray level in the z-axis direction can be smoothed.

In the above example, the pixel size ratio between the images is an odd multiple. That is, the kernel size corresponds to an odd number of pixels in each of the axis directions in the second image. An example in which the pixel size ratio between images is an even multiple is described below. For example, if the pixel sizes of the first image in the x-, y-, and z-axis directions are 0.5 mm, 0.5 mm, and 4 mm, and the pixel sizes of the second image are 0.5 mm, 0.5 mm, and 1 mm, the kernel size corresponds to 1×1×4 pixels in the second image. In general, when performing a filtering process using a kernel, the kernel size in an axis direction is set so as to correspond to an odd number of pixels, and the process is performed by using the pixel to be subjected to the filtering process and the same number of pixels located from the pixel in the positive direction and the negative direction (in the case of a kernel size corresponding to 5 pixels, 2 pixels in each direction). However, if the kernel size corresponds to an even number of pixels, such as 4 pixels, the same number of pixels cannot be used in the positive and negative directions. Accordingly, the resolution of the second image is converted to generate an image such that the pixel size of the first image is an odd multiple of that of the second image. More specifically, the pixel size of the second image is converted such that the pixel size of the first image is an odd multiple of the pixel size of the second image having the converted resolution and is the closest value that is less than or equal to the pixel size of the original second image. In the above example, the pixel size is an even multiple only in the z-axis direction. Accordingly, the resolution is converted only in the z-direction. That is, by converting the pixel sizes of the second image to 0.5 mm, 0.5 mm, and 0.8 mm, the kernel size becomes a size corresponding to 1×1×5 pixels in the image having the converted resolution. Thus, the gray level can be smoothed by using the same number of pixels in the positive and negative directions. At this time, the pixel size of the first image may be converted so as to be an odd multiple of that of the second image having a converted resolution and be a closest value that is smaller than or equal to the pixel size of the original first image.

According to the present embodiment, the gray level of the second image is approximately regarded as signal data, and the gray level of a smoothed image is calculated from the approximated signal data. It is desirable that the method for calculating the gray level from the signal data be similar to the method for actually generating the gray level of the first image and reconstructing an image. That is, if the first image reconstruction algorithm is known, the gray level of the smoothed image may be calculated in accordance with the algorithm.

In the above example, the case in which the first image has the first pixel size has been described. However, if the second image has the first pixel size, the first smoothed image can be acquired by smoothing the first image by the same technique.

Note that when calculating the value to be obtained by smoothing the gray levels of pixels within the range indicated by the kernel, all pixels within the range may be used, or the gray levels of pixels sampled at desired interval may be smoothed. The smoothing process can be sped up by sampling the pixels.

Note that according to the present embodiment, if the pixel sizes of the first image and the second image are the same or if the difference in pixel size is less than or equal to a threshold value, the first image and the second image may be output to the converted image acquisition unit 1020, and this step may be eliminated. In this case, the same processing as in the first embodiment is performed.

(S12020) (Acquisition of Converted Image)

As in the first embodiment, in step S12020, the converted image acquisition unit 1020 acquires the first converted image and the second converted image, where the first converted image is obtained by converting the resolution of the first image (or the first smoothed image) and the second converted image is obtained by converting the resolution of the second image (or the second smoothed image) such that the pixel sizes of the two images are the same. For example, if the first image has a first pixel size which is the larger one of the two pixel sizes and the second image has a second pixel size which is the smaller one of the two pixel sizes, the resolution conversion is performed such that the pixel size of the first image is converted so as to be the same as the second pixel size. Thereafter, the converted image acquisition unit 1020 outputs the generated converted image to the deformation information acquisition unit 1030, the position acquisition unit 1050, the comparison area setting unit 1060, the combination determination unit 1070, and the difference calculation unit 1080. Note that the converted image acquisition unit 1020 does not necessarily have to perform resolution conversion.

As described above, the processing is performed by the image processing apparatus 11000.

According to the present embodiment, for images having different pixel sizes, a smoothing process is performed such that the image having the smaller pixel size is subjected to the smoothing process so as to have the approximate larger pixel size. Subsequently, the difference is calculated. As a result, according to the present embodiment, the user can observe the difference image in which noise caused by the difference in pixel size is reduced more than in the first embodiment.

Note that according to the above-described embodiment, if the pixel size of the second image is smaller than that of the first image, the smoothing process is performed on the second image. However, the same effect can be obtained by the smoothing process performed on the second converted image. Similarly, if the pixel size of the first image is smaller than that of the second image, the smoothing process may be performed on the first converted image instead of performing on the first image. At this time, the kernel size for smoothing can be determined on the basis of the pixel size of the original image instead of the pixel size of the converted image.

Note that the same processing as in the present embodiment can be performed in the second to fifth embodiments. That is, after the image data is acquired, a smoothed image is generated by smoothing one of the first image and the second image having the smaller pixel size so that the smoothed image has the larger pixel size. Subsequently, the original image is replaced with the smoothed image, and the subsequent processing is performed. In this manner, the same noise reduction effect can be obtained. Note that according to the third embodiment, if the pixel size of the second image is smaller than that of the first image, a smoothed image may be generated by performing the smoothing process on the second deformation transformation image, and the second deformation transformation image may be replaced with the smoothed image. Furthermore, in each of the embodiments, the first image and the second image (or the converted images thereof) that have not been smoothed may be used in the deformation information acquisition process performed by the deformation information acquisition unit 1030, and the smoothed image (or the converted image thereof) may be used only in the difference value calculation process performed by the difference calculation unit 1080.

(Modification 6-1) (Acquiring Deformation Information from Outside)

According to the present embodiment, the deformation information is obtained by using the image subjected to the smoothing process. However, if the same conversion process was previously performed to obtain the deformation information, the deformation information obtained through the deformation process may be stored in the data server 110. Thereafter, the deformation information obtained in advance may be retrieved from the data server 110. In this configuration, the process to acquire the deformation information may be skipped. Subsequently, a difference image may be generated between the first image or the first converted image and the second smoothed image. For example, if a user who observes the difference image generated by the image processing apparatus according to the first embodiment determines that noise generated due to the difference in pixel size needs to be reduced, the user can generate a noise-reduced difference image by the image processing apparatus according to the present embodiment that uses the already acquired deformation information. As a result, the process of acquiring the deformation information can be skipped and, thus, the processing can be sped up.

(Modification 6-2) (Smoothing Method Without Using Pixel Division)

According to the present embodiment, an image is obtained by converting the resolution of the second image such that the pixel size of the first image is an odd multiple of the pixel size of the second image, and the obtained image is smoothed. However, the resolution does not necessarily have to be converted. For example, a first area having a pixel size the same as the first image is set around the pixel to be smoothed in the second image, and a smoothing process may be performed on the basis of the gray level of the pixel and the volume ratio of the pixel included in the first area. More specifically, if a pixel of the second image is completely included in the first area, the weighting coefficient related to the gray level of the pixel is set to 1. In contrast, for a pixel only half of which is included in the first area, the weighting coefficient related to the gray level is set to 0.5. Thus, a second smoothed image having the gray level equal to the weighted average value of the gray levels of all the pixels included in the first area can be acquired. According to the technique, the same effect can be obtained without converting the resolution of the second image such that the pixel size of the first image is an odd multiple of the pixel size of the second image.

Seventh Embodiment

An image processing apparatus according to the present embodiment is an apparatus that generates a three-dimensional difference image between a first image and a second image, as in the sixth embodiment. However, the image processing apparatus according to the present embodiment automatically determines the greater-lesser relationship between the pixel sizes of the images. If the pixel sizes of the images are different, the image processing apparatus acquires the size of the comparison area on the basis of the larger pixel size. As a result, the image processing apparatus generates a difference image having reduced noise for a smoothed image, as compared with the sixth embodiment. The image processing apparatus according to the present embodiment is described below.

Figure 13:
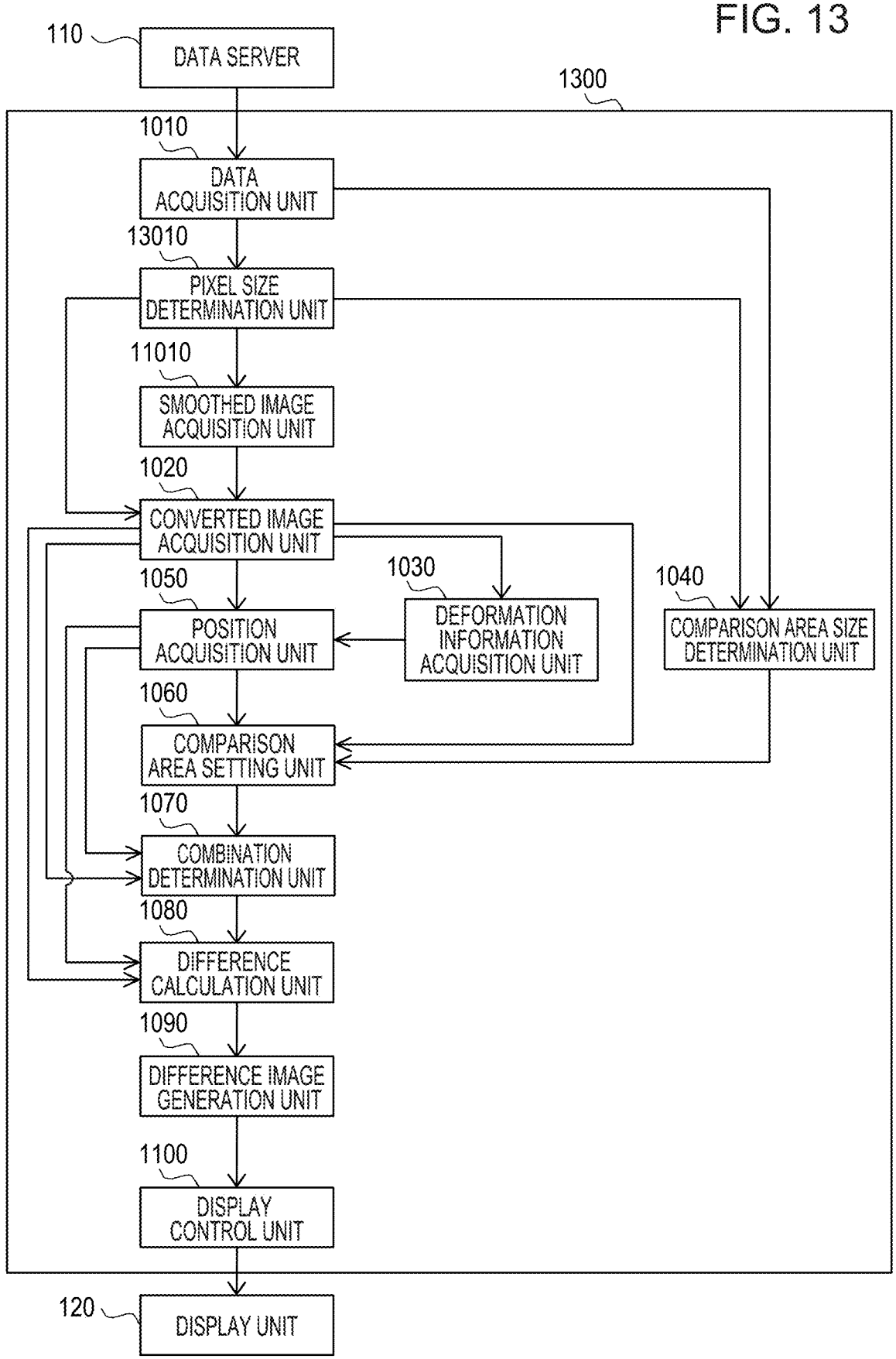
FIG. 13 is a diagram illustrating an example of the device configuration of an image processing apparatus according to a seventh embodiment.

FIG. 13 illustrates the configuration of the diagnostic imaging system according to the present embodiment. The functions of a pixel size determination unit 13010 and a smoothed image acquisition unit 11010 are described below. The other configurations have the same functions as those of the sixth embodiment and, thus, the description of the configurations is not repeated.

The pixel size determination unit 13010 automatically determines the greater-lesser relationship between the pixel sizes of the first image and the second image and acquires the larger pixel size as the first pixel size. That is, the pixel size determination unit 13010 determines whether the pixel sizes of the first image and the second image are different. If the pixel size of the second image is smaller than the pixel size of the first image as a result of the determination made by the pixel size determination unit 13010, the smoothed image acquisition unit 11010 acquires a second smoothed image obtained by smoothing the second image. However, if the pixel size of the first image is smaller than the pixel size of the second image, the smoothed image acquisition unit 11010 acquires a first smoothed image obtained by smoothing the first image.

Figure 14:
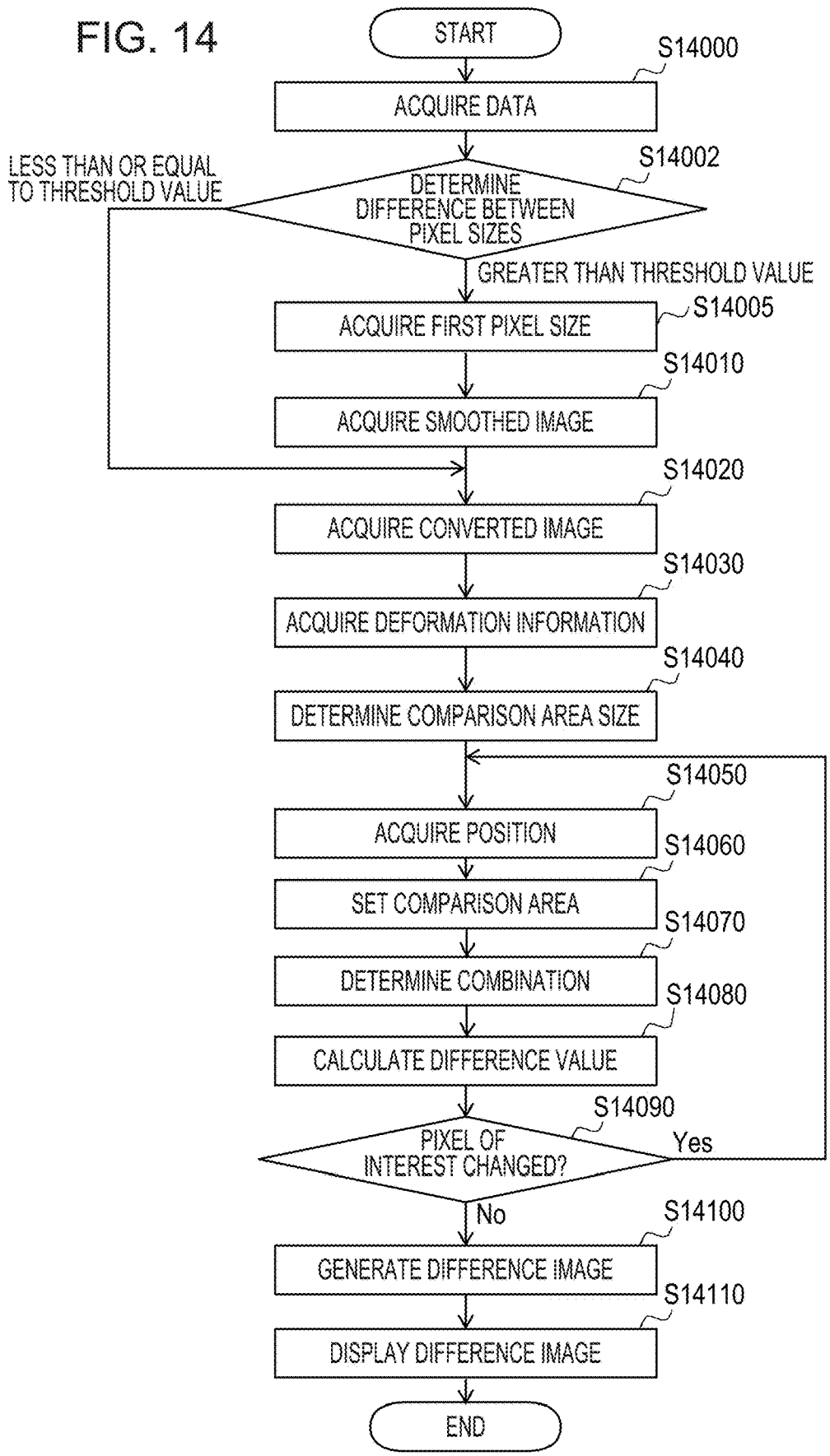
FIG. 14 is a flow diagram illustrating an example of the overall processing procedure according to the seventh embodiment.

FIG. 14 illustrates a flowchart of the overall processing procedure performed by an image processing apparatus 1300. Since the processes performed in steps S14020, S14030, S14050, and S14070 to S14110 are the same as those in steps S12020, S12030, S12050, and S12070 to S12110 of the sixth embodiment, respectively, description of the processes is not repeated. Only the differences from the flowchart illustrated in FIG. 12 are described below.

(S14000) (Data Acquisition)

In step S14000, the data acquisition unit 1010 acquires the first image and the second image input to the image processing apparatus 1300. In addition, the data acquisition unit 1010 acquires information regarding the pixel sizes of the first image and the second image in a predetermined axis direction. That is, the data acquisition unit 1010 corresponds to an example of image acquisition means for acquiring the first image and the second image. Furthermore, the data acquisition unit 1010 corresponds to an example of pixel size acquisition means for acquiring a first pixel size and a second pixel size that differs from the first pixel size which are the pixel sizes of a first image and a second image in a predetermined direction, respectively. The first image and the second image are captured at different points in time. Thereafter, the data acquisition unit 1010 outputs, to the pixel size determination unit 13010, the acquired first image, second image, and information regarding the pixel sizes of the first image and the second image. In addition, the data acquisition unit 1010 outputs, to the comparison area size determination unit 1040, the information regarding the pixel sizes of the first image and the second image. At this time, the data acquisition unit 1010 may output, to the comparison area size determination unit 1040, only the information about the pixel size of each of the first image and the second image in the predetermined axis direction. For example, the data acquisition unit 1010 outputs only the pixel size in the z-axis direction to the comparison area size determination unit 1040. Note that while the present embodiment is described with reference to the image processing apparatus 1300 including the function of 1010 to 1100, the image processing apparatus 1300 is not limited thereto.

(S14002) (Determination of Difference in Pixel Size)

In step S14002, the pixel size determination unit 13010 automatically determines whether the pixel sizes of the first image and the second image are different and determines the greater-lesser relationship between the pixel sizes of the first image and the second image. That is, the pixel size determination unit 13010 corresponds to an example of determination means that determines whether the first pixel size and the second pixel size acquired by the pixel size acquisition means are different. The pixel size determination unit 13010 further determines whether the difference in pixel size between the first image and the second image is greater than a threshold value. If the difference in pixel size is greater than the threshold value, the processing proceeds to step S14005. However, if the difference in pixel size is less than or equal to the threshold value, the pixel size determination unit 13010 outputs the first image and the second image to the converted image acquisition unit 1020, and the processes in steps S14005 and S14010 are skipped. In this case, the same processing as in the first embodiment is performed.

For example, it is determined whether at least one of differences in pixel size in the x-, y-, and z-axes (a value indicating a difference between the first pixel size and the second pixel size) is greater than a threshold value. At this time, the threshold value may be set as the ratio of the first pixel size to the second pixel size (for example, 1.5) or as a size difference (for example, 3 mm). Alternatively, any method for comparing two numerical values may be used. Note that a determination condition without using the above-described threshold value may be used for determining whether the pixel sizes are different.

According to the present embodiment, it is determined whether the difference in pixel size between the first image and the second image is greater than the threshold value. However, the determination may be made on the basis of the volume size of one voxel, or the determination may be made on the basis of the pixel size in only a predetermined axis direction. For example, in the case of a widely used CT image, the pixel sizes in a slice plane (x-, y-axis direction) are sufficiently small, and the difference therebetween is small. For this reason, the determination regarding the difference in pixel size may be made on the basis of only the pixel size in the z-axis direction (the slice thickness).

(S14005) (Acquisition of First Pixel Size)

In step S14005, the pixel size determination unit 13010 acquires, as a first pixel size, the larger one of the pixel sizes of the first image and the second image acquired from the data acquisition unit 1010 and acquires, as a second pixel size, the smaller one. Thereafter, the pixel size determination unit 13010 outputs the acquired first pixel size to the smoothed image acquisition unit 11010 and the comparison area size determination unit 1040.

For example, the pixel size of one of the first image and the second image having the larger voxel volume is acquired as the first pixel size. Alternatively, the pixel size of the image having the larger pixel size in a predetermined axis direction (for example, the z-axis direction) may be acquired as the first pixel size. Note that in a widely used CT image, the z-axis direction corresponds to the body axis direction. Alternatively, the larger pixel size may be selected for each of the x-, y-, and z-axes, and the combination of the selected ones may be used as the first pixel size.

(S14010) (Acquisition of Smoothed Image)

In step S14010, the smoothed image acquisition unit 11010 acquires a smoothed image obtained by smoothing the first image or the second image on the basis of the first pixel size acquired in step S14005. More specifically, if the first image has the first pixel size, the same process as in step S12010 is performed. That is, the first pixel size is selected as the smoothing kernel size, and the second image is smoothed. Note that if the image having the larger pixel size varies in each of the x-, y-, and z-axes, the first image and the second image may be defined for each axis, and the smoothing process may be performed in the axis direction of the second image. However, if the first image has a second pixel size smaller than the first pixel size, the process may be performed so that the first image is smoothed. That is, the first pixel size is selected as the smoothing kernel size, and the first image is smoothed.

(S14040) (Determination of Comparison Area Size)

In step S14040, the comparison area size determination unit 1040 determines the size of the comparison area. If the first pixel size is acquired in step S14005, the comparison area size determination unit 1040 determines the size of the comparison area on the basis of the first pixel size. That is, comparison area size determination unit 1040 corresponds to an example of a decision unit that if the first pixel size differs from the second pixel size, decides, on the basis of a larger one of the first pixel size and the second pixel size, a size in a predetermined axis direction of a comparison area including a plurality of gray levels, the comparison area being compared to a gray level of a position of interest in one of the first image and the second image, and the comparison area existing in the other of the first image and the second image, different from the one image. The comparison area size determination unit 1040 outputs the determined size of the comparison area to the comparison area setting unit 1060.

For example, the comparison area size determination unit 1040 determines only the size of the comparison area in the predetermined axis direction on the basis of the first pixel size. In a widely used CT image, the resolution (=the pixel size in the x and y directions) in a slice is often sufficient, so that a configuration may be employed that does not determine a comparison area in the x and y directions on the basis of the first pixel size. For example, in the x- and y-axis directions, the gray levels are compared only between the gray level at the position of interest of the first image and the gray level at the corresponding position of the second image. Alternatively, the size of the comparison area in the x- and y-axis directions may be set to a predetermined fixed value (for example, 1 mm), and only the size of the comparison area in the z-axis direction may be determined by the above-described method. In this manner, the calculation can be sped up. Still alternatively, in the x- and y-axis directions, as in the first embodiment, the comparison area size determination unit 1040 may select the sum of the half pixel sizes of the first image and the second image as the size of the comparison area. Note that the comparison area size determination unit 1040 may determine that the comparison area is 0 in the x- and y-axis directions so as to calculate only the difference between the gray level at the position of interest in the first image and the gray level at the corresponding position in the second image.

The reason why the size of the comparison area is acquired on the basis of the first pixel size is described below.

Figure 15:
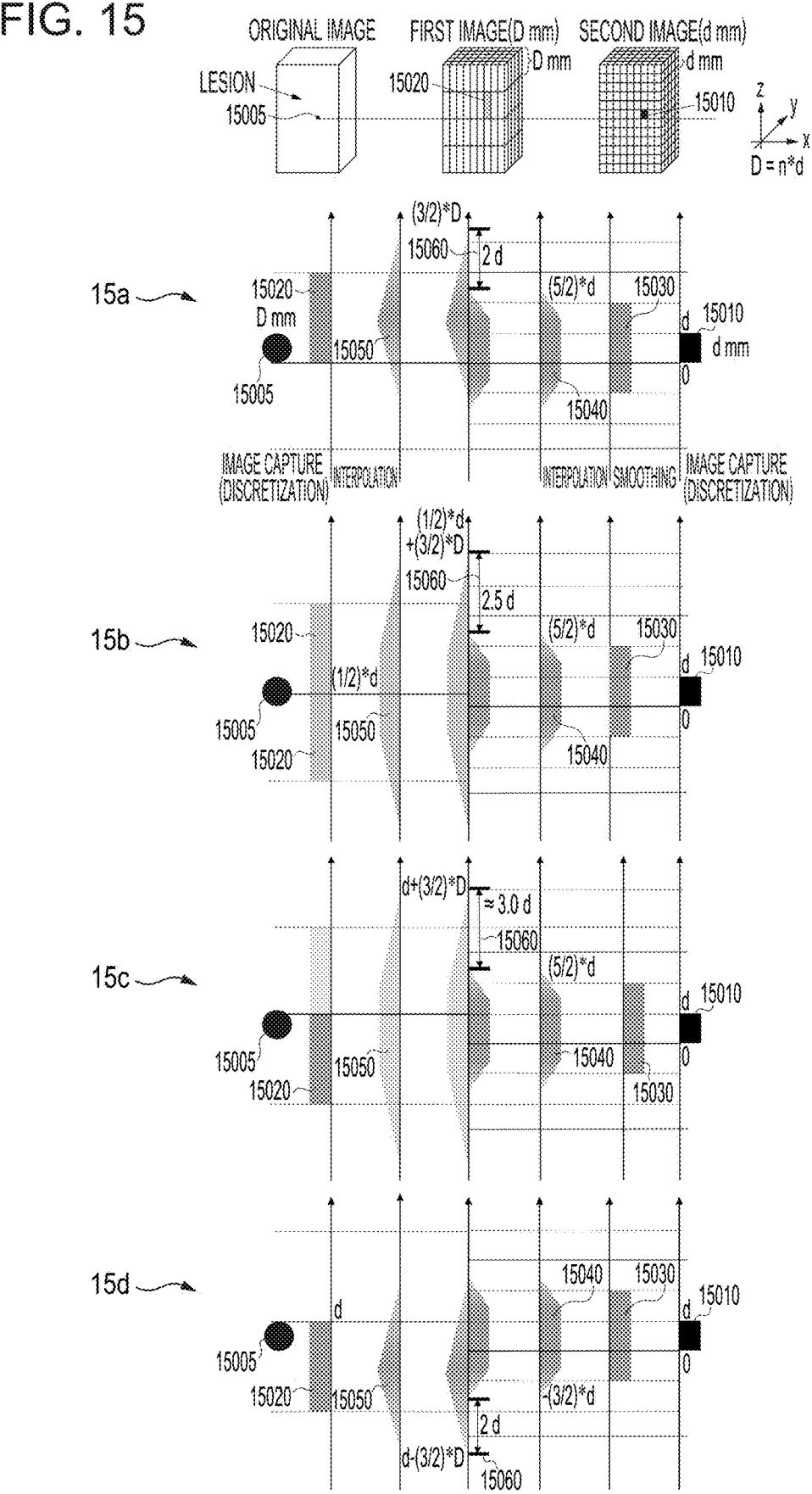
FIG. 15 is a diagram illustrating an example of the shift of a discretized position according to the seventh embodiment.

For example, it is assumed that the predetermined axis direction is the z-axis, a first image having a first pixel size and a second image having a second pixel size are present, and the first and second pixel sizes are D mm and d mm (D=n*d), respectively. FIG. 15 illustrates an example of the variation of the difference in the coordinates of the end points of the graphs when the discretized position of the first image is shifted while focusing on the pixel that reflects the same lesion in the first image and the second image having different pixel sizes. For simplicity of description, D=3*d, and the lesion in the original image is denoted as a sphere having a diameter of d mm. However, the size of the first pixel size, and the shape and the size of the lesion are not limited to the above-described ones. Note that in FIG. 15, the first image and the second image are, for example, images of the body, and the z-axis direction, which is the predetermined axis direction, indicates the body axis direction. That is, the pixel size in the z-axis direction indicates the slice thickness. Note that the processing according to the present embodiment is not limited to the processing in the z-axis direction and can be applied to pixels in each of the x and y direction.

(1) Case where Bottoms of Discretized Positions of Two Pixels are Registered

FIG. 15(15*a*) is a schematic illustration of an example of the case where bottom ends of discretized positions of two pixels are registered. In FIG. 15(15*a*), the ordinate represents the position in the z-axis direction.

A first image and a second image obtained by capturing (discretizing) the original image are acquired first. This step corresponds to step S14000 according to the present embodiment. Graphs 15010 and 15020 illustrate the pixel values of the pixels of the second image obtained by discretizing a lesion 15005 of the original image and the pixel values of the pixels in the first image, respectively. That is, the graphs 15010 and 15020 illustrate the gray level of a first pixel of the first image and the gray level of a second pixel of the second image representing a predetermined region of an object, respectively. Note that the graph 15010 represents a pixel that most reflects the lesion 15005 of the original image among the pixels of the second image of the two images. In contrast, the graph 15020 is the pixel that most reflects the lesion 15005 of the original image among the pixels of the first image. Note that reference numeral 15005 may denote not only a lesion but a structure such as a bone.

Subsequently, the smoothed image acquisition unit 11010 performs a smoothing process corresponding to step S14010 according to the present embodiment. A graph 15030 illustrates a value obtained by smoothing the gray level of the graph 15010 on the basis of the pixel size of the first image. More specifically, the kernel size is set to the pixel size of the first image, and a value obtained by smoothing the gray level of the second image is illustrated. That is, the smoothed image acquisition unit 11010 corresponds to an example of smoothing means that performs smoothing on an image having the smaller one of the first pixel size and the second pixel size by using a kernel size based on the larger pixel size.

Subsequently, the converted image acquisition unit 1020 interpolates the gray level corresponding to step S14070 according to the present embodiment (step S12020 according to the sixth embodiment). Graphs 15040 and 15050 illustrate values obtained by linearly interpolating the gray levels of graphs 15030 and 15020 with adjacent pixels, respectively. That is, the graph 15050 corresponds to an example of a first interpolation value obtained by interpolation based on the gray level of the first pixel of the first image and the gray level of the pixel adjacent to the first pixel. Furthermore, the graph 15040 corresponds to an example of a second interpolation value obtained by interpolation based on the gray level of the second pixel obtained by smoothing the gray level of the second pixel of the second image by using the first pixel size and the gray level of a pixel adjacent to the pixel indicating the gray level of the second pixel after smoothing process. The height in the horizontal direction in the graphs 15040 and 15050 indicates the gray level. Note that an existing image processing technique can be used for the interpolation of the gray level. For example, nearest neighbor interpolation, linear interpolation, or cubic interpolation can be used. At this time, the coordinates of the end points in the positive direction of the z-axis are (5/2)*d in the graph 15040 and (3/2)*D in the graph 15050.

In this case, a difference 15060 between the coordinates of the end points of the above-described graphs is {(3/2)*D−(5/2)*d}=2*d.

(2) Case where Lesion 15005 of Original Image is Discretized at Center in First Image FIG. 15(15*b*) is a schematic illustration of an example in which the lesion of the original image is discretized at the center in the first image. In FIG. 15(15*b*), the ordinate represents the position in the z-axis direction.

In this case, since the object is discretized at the center, the graph 15020, which is the pixel that most reflects the lesion 15005 of the original image among the pixels of the first image, extends over two pixels.

Subsequently, when linear interpolation is performed on these two pixels 15020 as in FIG. 15(15*a*), the coordinate of the end point in the positive direction of the z-axis of the graph 15050 is {(1/2)*d+(3/2)*D}=(5/3)*D. At this time, the difference 15060 between the coordinates of the end points of the two graphs is {(5/3)*D−(5/2)*d}=2.5*d.

(3) Case where Lesion 15005 of Original Image is Discretized at End in First Image FIG. 15(15*c*) is a schematic illustration of an example in which the lesion in the original image is discretized at the end (the upper end) in the first image. In FIG. 15(15*c*), the ordinate represents the position in the z-axis direction. Note that in FIG. 15(15*c*), it is assumed that the lesion is discretized at an end portion d' (<d) that is infinitely close to the contact point (z=d) of the lesion 15005 in the original image.

In this case, since the object is discretized at the end portion, the graph 15020, which is a pixel that includes a more portion of lesion in the discretized section among the two pixels that reflect the lesion 15005 in the original image, is the pixel that most reflects the lesion 15005.

Subsequently, the two pixels reflecting the lesion 15005 in the original image are subjected to linear interpolation. At this time, the coordinate of the end point in the positive direction of the z-axis in the graph 15050 is $\{d'+(3/2)*D\}$ $(<\{d+(3/2)*D\}=(11/6)*D)$. More specifically, the value is reduced by the shift amount between the discretized positions of the first image and the second image. However, in FIG. 15(15*c*), it is assumed that the shift amount of the discretized position is infinitely small. Therefore, this value can be approximated to 0. In this case, the difference 15060 between the coordinates of the end points of the two graphs is $\{(11/6)*D-(5/2)*d\}\approx 3*d$. This value is the same as the first pixel size.

(4) Case where Upper Ends of Discretized Positions of Two Pixels are Registered

FIG. 15(15*d*) is a schematic illustration of an example of the case where the upper ends of the discretized positions of two pixels are registered. In FIG. 15(15*d*), the ordinate represents the position in the z-axis direction.

The processing is performed in the same manner as in FIG. 15(15*a*). As a result of comparison of the coordinates of the end points of the graphs 15040 and 15050, the difference 15060 is $|[\{d-(3/2)*D\}-\{-(3/2)*D\}]|=|-(2*d)|=2*d$.

Therefore, as can be seen from 15*a* to 15*d* in FIG. 15, the difference between the coordinates of the end points is maintained in the range of $2*d$ to $3*d$ when linear interpolation based on the pixel that most reflects the lesion 15005 in the original image and the adjacent pixels is performed. Consequently, by setting the size of the comparison area to $3*d=D$, that is, by adaptively setting the size of the comparison area to the first pixel size, the gray level reflecting the lesion 15005 in the original image can be searched for between the two images with the minimum required size of the comparison area. From a different point of view, by setting, in one of the first image and the second image, a comparison area of the size based on a shift amount between a position corresponding to a value other than the maximum one of the first interpolation value (graph 15050) and a position corresponding to a value other than the maximum one of the second interpolation value (graph 15040), a value corresponding to a value other than the maximum one of the interpolation value can be searched for. Note that the shift amount between the minimum one of the first interpolation value and the minimum one of the corresponding second interpolation value is the largest, and the size of the comparison area may be determined on the basis of this shift amount. Alternatively, the size of the comparison area may be determined on the basis of the shift amount between a value other than the maximum and the minimum of the first interpolation value and a corresponding value other than the maximum and the minimum of the second interpolation value.

The comparison area size determination unit 1040 may determine the size of the comparison area by multiplying the first pixel size (the larger pixel size) by a predetermined coefficient. The predetermined coefficient may be 0.5 or another value. According to the present embodiment, the predetermined coefficient is set to 0.5 because the degree of separation between the first interpolation value and the second interpolation value is a random value and, thus, each of the above-described various cases occurs randomly.

As can be seen from the processes in steps S14002, 14005, and 14010, if the value indicating the difference between the first pixel size and the second pixel size is greater than or equal to a threshold value, the comparison area size determination unit 1040 determines the size of the comparison area in a predetermined axis direction on the basis of the larger one of the pixel sizes.

However, if the first pixel size is not acquired in step S14005, the comparison area size determination unit 1040 determines the size of the comparison area on the basis of, for example, the pixel sizes of the first image and the second image, as in the sixth embodiment. More specifically, the comparison area size determination unit 1040 determines that the size of the comparison area is the sum of the half pixel size of the first image and the half pixel size of the second image. That is, if the value indicating the difference between the first pixel size and the second pixel size is less than the threshold value, the comparison area size determination unit 1040 determines the comparison area size in the predetermined axis direction on the basis of the first pixel size and the second pixel size.

Note that if the first pixel size is not acquired in step S14005, the comparison area size determination unit 1040 may determine that the comparison area is 0 so that only the difference between the gray level at the position of interest in the first image and the gray level at the corresponding position in the second image is calculated. Thereafter, the comparison area size determination unit 1040 outputs the determined size of the comparison area to the comparison area setting unit 1060. Note that as in the above-described embodiment, the comparison area size determination unit 1040 may determine the comparison area size by multiplying the first pixel size (the larger pixel size) by a predetermined coefficient. The predetermined coefficient may be 0.5 or another value. According to the present embodiment, the predetermined coefficient is set to 0.5 because the degree of separation between the first interpolation value and the second interpolation value is a random value and, thus, each of the above-described various cases occurs randomly. Furthermore, if, in S14002, it is determined that the difference between the two pixel sizes is greater than the threshold value, this step S14040 is not limited to the above-described processing procedure and may be performed before any one of S14030, S14020, and S14010.

(S14060) (Setting of Comparison Area)

In step S14060, the comparison area setting unit 1060 sets the comparison area having a size of the comparison area determined in step 14040 on the basis of the corresponding position in the second image. For example, the comparison area is set on the basis of the corresponding position in the smoothed image. The area in which the comparison area is set is not limited to the second image. For example, when the position of interest is set in the second image, the comparison area may be set in the first image on the basis of the corresponding position in the first image that corresponds to the position of interest. The comparison area setting unit 1060 corresponds to an example of setting means for setting a comparison area in the other image on the basis of the corresponding position in the other image. For example, the comparison area setting unit 1060 performs the setting around the corresponding position in the second image. That is, the comparison area setting unit 1060 sets the comparison area having a size decided by the decision means around the corresponding position in the other image. At this time, the comparison area may be set so as not to exceed the position away from the corresponding position by the first pixel size in at least one of the three-dimensional axis directions of x, y, and z. That is, in an n-dimensional image, the comparison area setting unit 1060 sets a comparison area such that the comparison area does not exceed the position away from the corresponding position in the other image by the larger pixel size in at least one of the n dimensional axis directions.

For example, assume that a rectangular comparison area is set around the corresponding position in the second image. It is assumed first that the coordinates of the corresponding position are (x, y, z)=(1, 1, 1), and the size D of the comparison area is 4. At this time, if the center of the comparison area is set to (x, y, z)=(1, 1, 2), the coordinates of the end point of the rectangular comparison area are (x, y, z)=(1+4, 1+4, 2+4)=(5, 5, 6). The coordinates exceed the position (z=5) away from the corresponding position by the first pixel size in the z direction, but does not exceed the position (x=5, y=5) away from the corresponding position by the first pixel size in the x and y directions. Accordingly, this comparison area corresponds to a comparison area that does not exceed the position away from the corresponding position by the first pixel size in at least one of the axis directions. Alternatively, the comparison area may be set so as not to exceed the position away from the corresponding position by the first pixel size in all three axis directions. Thereafter, the information regarding the set comparison area is output to the difference calculation unit 1080.

According to the present embodiment, when the smoothing process is performed on the second image by using a kernel having the same size as the first pixel size, the smoothed image obtained by smoothing the second image can be considered as an image that is discretized in an area having the same size as the first pixel size, as in the first image. That is, since the discretized position of the smoothed image is shifted from that of the first image by a maximum of half pixel size of the first pixel size, the size of the comparison area is set to a large pixel size (=a half of the first pixel size+a half of the first pixel size). In this manner, noise generated due to the discretized position shift between the smoothed image and the first image can be reduced.

The size of the comparison area in the x and y directions, each of which is not the predetermined axis direction, can be set to a predetermined value. For example, more specifically, the comparison area size determination unit 1040 may set the size of the comparison area in each of the x and y directions to the sum of a half of the pixel size of the first image and a half of the pixel size of the second image in the corresponding direction, or a predetermined constant value. Alternatively, the comparison area size determination unit 1040 may set the size of the comparison area in each of the x and y directions, which is not the predetermined axis direction, to 0 so that the gray level at the position of interest is compared with only the gray level at the corresponding position.

(S14070) (Determination of Combination)

In step S14070, the combination determination unit 1070 determines a combination of gray levels to be subjected to a comparison process (calculation of the difference). First, the combination determination unit 1070 interpolates the gray level at the position of interest in the first converted image and the gray level of the pixel in the comparison area of the second converted image (the positions are acquired in step S14050). Note that to interpolate the gray levels, an existing image processing technique can be used. For example, nearest neighbor interpolation, linear interpolation, or cubic interpolation can be used. Also note that the gray levels of the pixels in the comparison area of the second converted image do not necessarily have to be interpolated. The combination of the gray levels may be determined so that the difference between the gray level at the position of interest in the first converted image and the gray levels of all the pixels in the comparison area of the second converted image are calculated. Alternatively, at least one pixel may be sampled from among the pixels included in the comparison area, and the combination of the gray level of the pixel and the gray level at the position of interest may be selected as the combination to be subjected to difference calculation. For example, the combination determination unit 1070 samples the maximum gray level and the minimum gray level from among the pixels included in the comparison area. Thereafter, the combination determination unit 1070 selects the combination of the maximum gray level included in the comparison area and the gray level at the position of interest and the combination of the minimum gray level included in the comparison area and the gray level at the position of interest as the combinations to be subjected to difference calculation. Note that the gray levels to be sampled are not limited to the maximum and minimum values, and three or more values may be sampled, or only one value, such as the maximum gray level or the minimum gray level, may be sampled. Alternatively, the combination determination unit 1070 may acquire the gray level range having the maximum gray level and the minimum gray level (the upper limit value and lower limit value) at both ends in the comparison area and acquire, as the combination to be subjected to difference calculation, the gray level at the position of interest and the gray level range in the comparison area. The gray level range in the comparison area may be other than the maximum and minimum gray levels. For example, the maximum value and the minimum value after removing the outlier of the gray level may be used.

The combination determination unit 1070 outputs, to the difference calculation unit 1080, information indicating the determined combination of the gray levels to be subjected to difference calculation. For example, as described above, the difference calculation unit 1080 calculates the difference between the gray level at the position of interest in one image and the gray levels at a plurality of positions in the comparison area of the other image. The information indicating the combination of the gray levels output from the combination determination unit 1070 may include all the combinations of the gray levels of the position of interest in the first converted image and the gray levels of the pixels in the comparison area of the second converted image. Alternatively, only the information may be output that indicates the combination of the gray level of the pixel sampled from among the pixels included in the comparison area and the gray level at the position of interest.

As described above, the processing is performed by the image processing apparatus 1300.

According to the present embodiment, if the pixel sizes of images are different, the greater-lesser relationship between the pixel sizes is automatically determined, and a smoothing process is performed so that the image with the smaller pixel size is approximated to the image having the larger image, and the smoothed image is acquired. In this manner, it can be considered that each of the smoothed image and the first image is discretized in an area having the same size as the first pixel size. Thereafter, by using a value based on the size of the discretized area (the first pixel size) as the size of the comparison area, the user can observe a difference image in which noise caused by the difference in pixel size is reduced, as compared with the sixth embodiment. That is, the comparison area size that can further reduce noise can be determined adaptively. In addition, according to the present embodiment, the size of the comparison area is determined on the basis of the first pixel size that is greater than the sum of the half pixel sizes of the two images. Consequently, even a relatively weak signal among signals representing a predetermined object is less likely to be imaged as noise.

Eighth Embodiment

Figure 16:
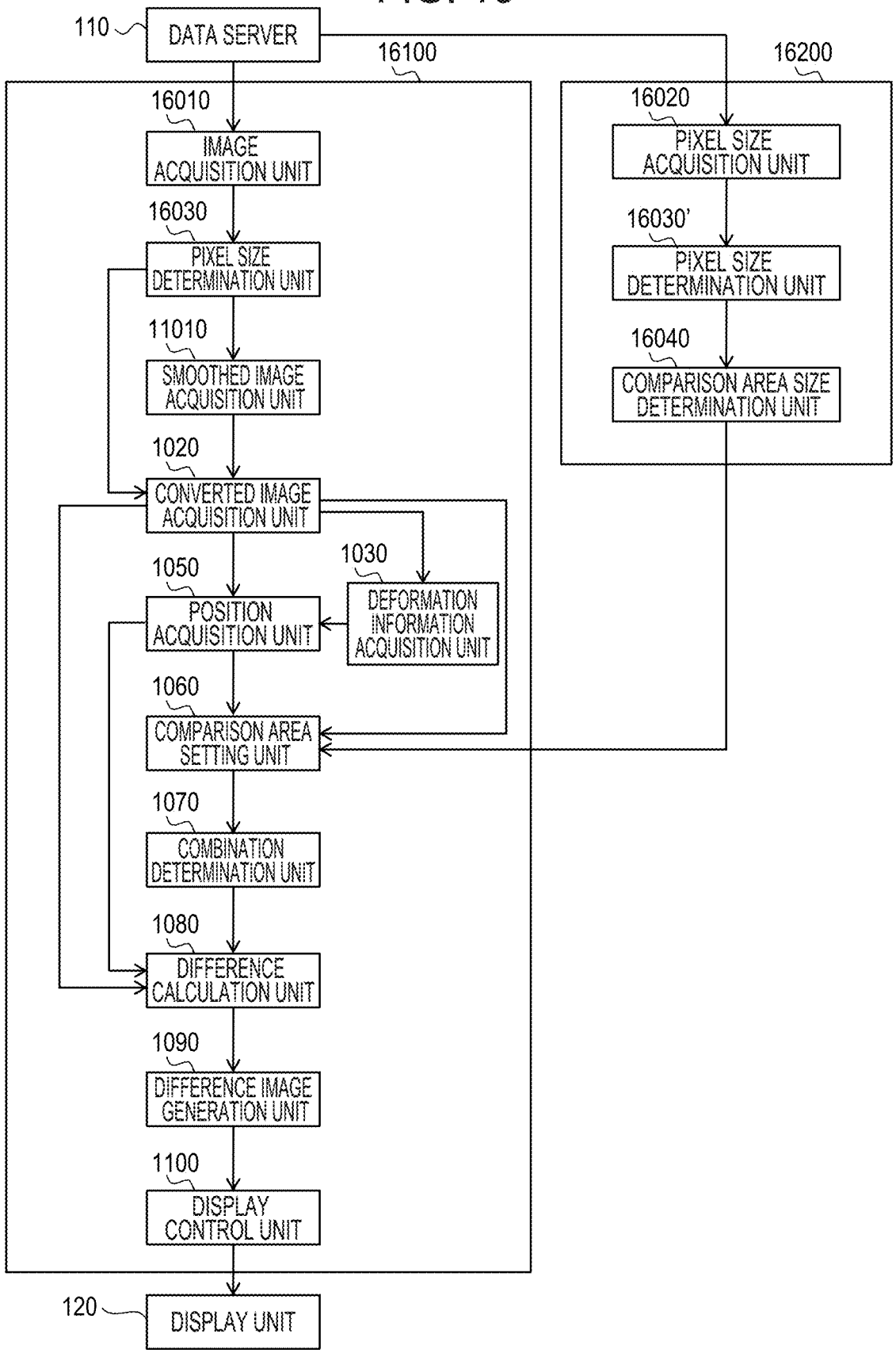
FIG. 16 is a diagram illustrating an example of the processing procedure performed by an image processing apparatus according to an eighth embodiment.

In the above-described embodiments, one image processing apparatus performs a series of processes from the process of acquiring two images captured at different points in time to the process of generating a difference image. However, the image processing described in this specification is performed even when the comparison area size determination unit 1040 is included in another image processing apparatus. FIG. 16 illustrates constituent elements provided in each of the two image processing apparatuses in this case. The functions of an image acquisition unit 16010, a pixel size acquisition unit 16020, a pixel size determination unit 16030, and a pixel size determination unit 16030' are described below. Descriptions of the other configurations are not repeated.

The image acquisition unit 16010 acquires a first image and a second image input from the data server 110 to an image processing apparatus 16100.

The pixel size acquisition unit 16020 acquires the first pixel size and the second pixel size input from the data server 110 to an image processing apparatus 16200. At this time, the pixel size determination unit 16020 need not acquire the first image and the second image themselves.

The pixel size determination unit 16030 determines the greater-lesser relationship between the pixel sizes of the first image and the second image input from the image acquisition unit 16010 and selects the larger pixel size as the first pixel size.

The pixel size determination unit 16030' determines the greater-lesser relationship between the two pixel sizes input from the pixel size acquisition unit 16020 and selects the larger pixel size as the first pixel size. At this time, in the two apparatuses, only the pixel size determination unit 16030 may determine the greater-lesser relationship between the two pixel sizes and transmits the result of determination to the other image processing apparatus 16200. Alternatively, only the pixel size determination unit 16030' may determine the greater-lesser relationship between the two pixel sizes and transmit the result of determination to the separate image processing apparatus 16100.

Figure 17:
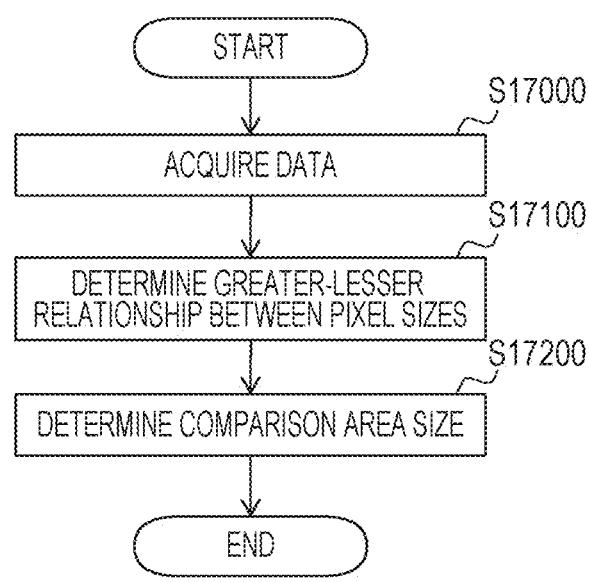
FIG. 17 is a flow diagram illustrating an example of a technique for setting a comparison area according to the eighth embodiment.

FIG. 17 is a flowchart of the overall processing procedure performed by the image processing apparatus 16200.

Each of the processes is described below.

(S17000) (Data Acquisition)

In step S17000, the pixel size acquisition unit 16020 outputs, to the pixel size determination unit 16030', information regarding the pixel size of the first image and the pixel size of the second image, which are input to the image processing apparatus 16200.

(S17100) (Determining Greater-Lesser Relationship Between Pixel Sizes)

In step S17100, the pixel size determination unit 16030' acquires, as the first pixel size, the larger one of the pixel size of the first image and the pixel size of the second image acquired from the pixel size acquisition unit 16020 and acquires, as the second pixel size, the smaller one. Thereafter, the pixel size determination unit 16030' outputs the acquired first pixel size to a comparison area size determination unit 16040.

For example, among the first image and the second image, the pixel size of one having the larger volume of a voxel is acquired as the first pixel size. Alternatively, the pixel size of the image having the larger pixel size in the predetermined axis direction (for example, the z-axis direction) may be acquired as the first pixel size. Note that in widely used CT images, the z-axis direction corresponds to the body axis direction. Still alternatively, the larger pixel size may be selected for each of the x-, y-, and z-axes, and the combination of the larger pixel sizes may be used as the first pixel size.

(S17200) (Determining Size of Comparison Area)

In step S17200, the comparison area size determination unit 16040 determines the size of the comparison area. If the first pixel size is acquired in step S17200, the comparison area size determination unit 16040 determines the size of the comparison area on the basis of the first pixel size.

Thereafter, the comparison area size determination unit 16040 outputs the size of the comparison area to the comparison area setting unit 1060 of the image processing apparatus 16100.

Ninth Embodiment

According to the above-described embodiments, the case has been described where the difference calculation unit 1080 and the difference image generation unit 1090 generate a difference image. The image generated by the image processing apparatus according to the present invention is not limited to a difference image as long as the image represents the difference between two images captured at different points in time. For example, the image processing apparatus may calculate the ratio between the gray levels of two images and generate an image illustrating the ratio of gray levels between the two images (the result of division) on the basis of the calculated ratio. In this case, the ratio has a value of 1 in a part having no change, and the ratio has a value other than 1 in a part having any change, so that a change over time can be imaged in a similar manner to the difference image described above. Note that if an image illustrating the ratio between gray levels is generated, a ratio calculation unit for calculating the ratio and an image generation unit for generating the image illustrating the ratio can be provided instead of the difference calculation unit 1080 and the difference image generation unit 1090, respectively. In this case, since it can be said that each of the calculation of the difference between a plurality of gray levels and the calculation of the ratio between the plurality of gray levels is the same as comparison of the plurality of gray levels, the difference calculation unit 1080 and the ratio calculation unit can be collectively referred to as a comparison unit. That is, the difference calculation unit 1080 or the ratio calculation unit corresponds to an example of comparison means for comparing the gray level at the position of interest in one image with the gray levels at a plurality of positions in the comparison area of the other image.

As argued above, according to each of the embodiments, an appropriate size of the comparison area can be determined.

Other Embodiments

Furthermore, the technology disclosed in the present specification can be implemented as a system, a device, a method, a program, a recording medium (a storage medium), or the like. More specifically, the technology may be applied to a system including a plurality of devices (for example, a host computer, an interface device, an image capture device, and a web application) or may be applied to a device including a single device.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a memory storing program; and
one or more processors which, by executing the program, function as:
a pixel size acquisition unit configured to acquire a first pixel size and a second pixel size that are pixel sizes in a predetermined axis direction of a first image and a second image captured at different points in time, respectively;
a determination unit configured to determine whether the first pixel size and the second pixel size acquired by the pixel size acquisition unit differ from each other; and
a decision unit configured to, if the first pixel size differs from the second pixel size, decide, on the basis of a larger one of the first pixel size and the second pixel size, a size in a predetermined axis direction of a comparison area including a plurality of gray levels, the comparison area being compared to a gray level of a position of interest in one image of the first image and the second image, and the comparison area existing in another image of the first image and the second image, different from the one image.

2. The image processing apparatus according to claim 1, wherein the one or more processors, by executing the program, further function as:
an image acquisition unit configured to acquire the first image and the second image;
a position acquisition unit configured to acquire the position of interest in the one image and a corresponding position that corresponds to the position of interest in the other image;
a setting unit configured to set the comparison area of the other image on the basis of the corresponding position in the other image; and
a comparison unit configured to compare the gray level at the position of interest in the one image with the gray levels at a plurality of positions in the comparison area of the other image.

3. The image processing apparatus according to claim 2, wherein the comparison unit compares the difference between the gray level at the position of interest in the one image and the gray level at each of the plurality of positions in the comparison area of the other image.

4. The image processing apparatus according to claim 1, wherein the first image and the second image are images obtained by capturing the image of the body, and the predetermined axis direction is the direction of the axis of the body.

5. The image processing apparatus according to claim 1, wherein the one or more processors, by executing the program, further function as:
a smoothing unit configured to smooth the image having the smaller one of the first pixel size and the second pixel size by using a kernel size based on the larger pixel size.

6. The image processing apparatus according to claim 1, wherein the decision unit decides the size of the comparison area by multiplying the larger pixel size by a predetermined coefficient.

7. The image processing apparatus according to claim 6, wherein the predetermined coefficient is 0.5.

8. The image processing apparatus according to claim 1, wherein if a value indicating the difference between the first pixel size and the second pixel size is greater than or equal to a threshold value, the decision unit decides the size of the comparison area in the predetermined axis direction on the basis of the larger pixel size.

9. The image processing apparatus according to claim 8, wherein if the value indicating the difference between the first pixel size and the second pixel size is less than the threshold value, the size of the comparison area in the predetermined axis direction is decided on the basis of the first pixel size and the second pixel size.

10. The image processing apparatus according to claim 8, wherein the decision unit decides the size of the comparison area in an axis direction different from the predetermined axis direction to be a predetermined value.

11. The image processing apparatus according to claim 8, wherein the decision unit decides that comparison of gray levels is performed between the gray level at the position of interest and the gray level at the corresponding position in the axis direction different from the predetermined axis direction.

12. The image processing apparatus according to claim 2, wherein each of the first image and the second image is an n-dimensional image, and the setting unit sets the comparison area such that the comparison area does not exceed a position away from the corresponding position in the other image by the larger pixel size in at least one of the n-dimensional axis directions.

13. The image processing apparatus according to claim 2, wherein the setting unit set the comparison area having a size decided by the decision unit around the corresponding position in the other image.

14. The image processing apparatus according to claim 8, wherein the value indicating the difference between the first pixel size and the second pixel size is the ratio of the first pixel size to the second pixel size, and the threshold value is 1.5.

15. A diagnostic imaging system comprising: the image processing apparatus according to claim 1; and an image capture device, wherein the image capture device captures the first image and the second image, and the image processing apparatus acquires the first image and the second image.

16. The diagnostic imaging system according to claim 15, further comprising a data server configured to hold the first image and the second image captured by the image capture device.

17. The diagnostic imaging system according to claim 16, further comprising a monitor configured to display a difference image generated by using, as a gray level, a difference value compared and calculated by the comparison unit.

18. An image processing method comprising:
acquiring a first pixel size and a second pixel size that are pixel sizes in a predetermined axis direction of a first image and a second image captured at different points in time, respectively;
determining whether the first pixel size and the second pixel size acquired in the pixel size acquisition step differ from each other; and
if the first pixel size differs from the second pixel size, deciding, on the basis of a larger one of the first pixel size and the second pixel size, a size in a predetermined axis direction of a comparison area including a plurality of gray levels, the comparison area being compared to a gray level of a position of interest in one image of the first image and the second image, and the comparison area existing in another image of the first image and the second image, different from the one image.

19. A non-transitory computer-readable storage medium storing a program for causing a computer to execute an image processing method comprising:
acquiring a first pixel size and a second pixel size that are pixel sizes in a predetermined axis direction of a first image and a second image captured at different points in time, respectively;
determining whether the first pixel size and the second pixel size acquired in the pixel size acquisition step differ from each other; and
if the first pixel size differs from the second pixel size, deciding, on the basis of a larger one of the first pixel size and the second pixel size, a size in a predetermined axis direction of a comparison area including a plurality of gray levels, the comparison area being compared to a gray level of a position of interest in one image of the first image and the second image, and the comparison area existing in another image of the first image and the second image, different from the one image.

20. An image processing apparatus comprising:
a memory storing program; and
one or more processors which, by executing the program, function as:
a pixel size acquisition unit configured to acquire a first pixel size and a second pixel size that are pixel sizes in a predetermined axis direction of a first image and a second image captured at different points in time, respectively; and
a decision unit configured to, if the first pixel size differs from the second pixel size, decide, on the basis of a larger one of the first pixel size and the second pixel size, a size of a comparison area including a plurality of gray levels, the comparison area being compared to a gray level of a position of interest in one image of the first image and the second image, and the comparison area existing in another image of the first image and the second image, different from the one image.

21. The image processing apparatus according to claim 20, wherein the one or more processors, by executing the program, further function as:
an image acquisition unit configured to acquire the first image and the second image;
a position acquisition unit configured to acquire the position of interest in the one image and a corresponding position that corresponds to the position of interest in the other image;
a setting unit configured to set the comparison area in the other image on the basis of the corresponding position in the other image; and
a comparison unit configured to compare a gray level at the position of interest in the one image with a gray level at each of a plurality of positions in the comparison area of the other image and calculating a difference value.

22. The image processing apparatus according to claim 21, wherein the one or more processors, by executing the program, further function as a difference image generation unit configured to generate a difference image on the basis of the difference values.

23. The image processing apparatus according to claim 20, wherein the first image and the second image are images obtained by capturing the image of a body, and the predetermined axis direction is the direction of the axis of the body.

24. The image processing apparatus according to claim 20, wherein the one or more processors, by executing the program, further function as a smoothing unit configured to smooth the image having the smaller one of the first pixel size and the second pixel size.

25. The image processing apparatus according to claim 20, wherein if a value indicating the difference between the first pixel size and the second pixel size is greater than or equal to a threshold value, the decision unit decides the size of the comparison area in the predetermined axis direction on the basis of the larger pixel size.

26. The image processing apparatus according to claim 25, wherein if the value indicating the difference between the first pixel size and the second pixel size is less than the threshold value, the size of the comparison area in the predetermined axis direction is determined on the basis of the first pixel size and the second pixel size.

27. The image processing apparatus according to claim 25, wherein the decision unit decides the size of the comparison area in an axis direction different from the predetermined axis direction on the basis of pixel sizes of the first image and the second image in the axis direction different from the predetermined axis direction.

28. An image processing method comprising:
acquiring a first pixel size and a second pixel size that are pixel sizes in a predetermined axis direction of a first image and a second image captured at different points in time, respectively; and
if the first pixel size differs from the second pixel size, deciding, on the basis of a larger one of the first pixel size and the second pixel size, a size in a predetermined axis direction of a comparison area including a plurality of gray levels, the comparison area being compared to a gray level of a position of interest in one image of the first image and the second image, and the comparison area existing in another image of the first image and the second image, different from the one image.

* * * * *